United States Patent
Duncan

(10) Patent No.: US 9,283,371 B2
(45) Date of Patent: Mar. 15, 2016

(54) ELECTRO-STIMULATION SYSTEM

(76) Inventor: Thu-Ha Duncan, Cleveland, TN (US)

(*) Notice: Subject to any disclaimer, the term of this patent is extended or adjusted under 35 U.S.C. 154(b) by 74 days.

(21) Appl. No.: 13/408,481

(22) Filed: Feb. 29, 2012

(65) Prior Publication Data

US 2013/0226275 A1  Aug. 29, 2013

(51) Int. Cl.
*A61N 1/00* (2006.01)
*A61N 1/04* (2006.01)
*A61N 1/36* (2006.01)

(52) U.S. Cl.
CPC ............ *A61N 1/0492* (2013.01); *A61N 1/0456* (2013.01); *A61N 1/36014* (2013.01); *A61N 1/36021* (2013.01); *A61N 1/048* (2013.01)

(58) Field of Classification Search
CPC .. A61N 1/0492; A61N 1/0456; A61N 1/0452
USPC ..................................... 607/46, 152; 600/382
See application file for complete search history.

(56) References Cited

U.S. PATENT DOCUMENTS

| | | | |
|---|---|---|---|
| 4,706,680 A | 11/1987 | Keusch | |
| 5,336,255 A | 8/1994 | Kanare | |
| 5,352,315 A * | 10/1994 | Carrier et al. | 156/267 |
| 5,487,759 A | 1/1996 | Bastyr | |
| 5,540,735 A | 7/1996 | Wingrove | |
| 6,445,955 B1 * | 9/2002 | Michelson et al. | 607/46 |
| 6,609,018 B2 | 8/2003 | Cory | |
| 6,741,889 B1 | 5/2004 | Holcomb | |
| 6,847,836 B1 | 1/2005 | Sujdak | |
| 7,069,089 B2 | 6/2006 | Minogue | |
| 7,761,131 B2 | 7/2010 | Copp-Howland | |
| 2002/0151951 A1 | 10/2002 | Axelgaard | |
| 2006/0270942 A1 * | 11/2006 | McAdams | 600/547 |
| 2007/0060975 A1 | 3/2007 | Mannheimer | |
| 2009/0216294 A1 * | 8/2009 | Ewing et al. | 607/46 |
| 2010/0030299 A1 | 2/2010 | Covalin | |
| 2010/0036227 A1 * | 2/2010 | Cox et al. | 600/374 |
| 2010/0211122 A1 | 8/2010 | Hensley | |
| 2010/0228304 A1 * | 9/2010 | Kriksunov et al. | 607/3 |

FOREIGN PATENT DOCUMENTS

WO   WO 2007134288   5/2006

OTHER PUBLICATIONS

TENS Self-adhesive Electrode Pads, DIFTrade.com, Dec. 8, 2010; http://www.diytrade.com/china/4/products/7710000/Butterfly_TENS_Self-adhesive_Electrode_pads.html.
Redplacement Medical Conductive Gel for TENS Pad, Feb. 7, 2011; http://www.alibaba.com/product-gs/377296678/Replacement_Medical_conductive_gelfor_TENS.html.

* cited by examiner

*Primary Examiner* — Amanda Patton
*Assistant Examiner* — Philip Edwards
(74) *Attorney, Agent, or Firm* — Miller & Martin PLLC

(57) ABSTRACT

An electro-stimulation system is provided with a compact power and control assembly and a plurality of shaped gel electrode patches with instructions to facilitate user administration of therapy.

18 Claims, 30 Drawing Sheets

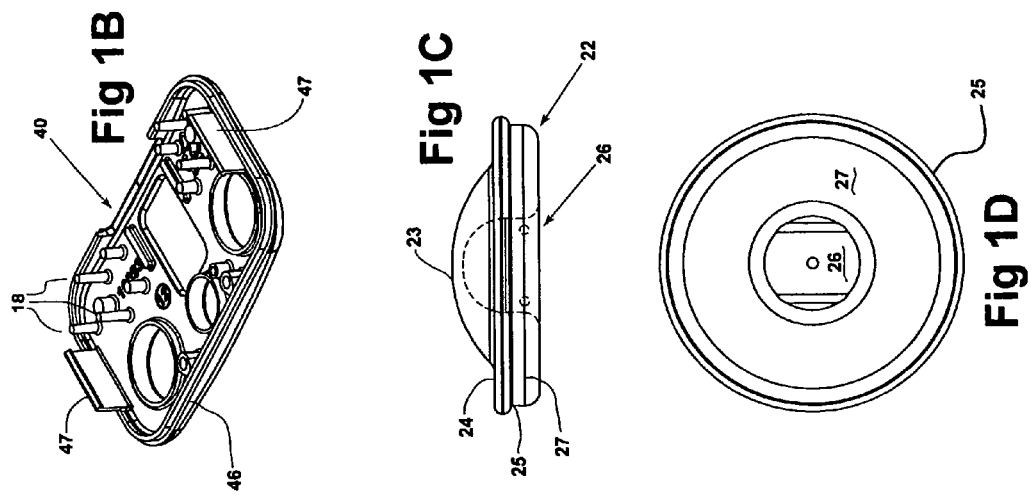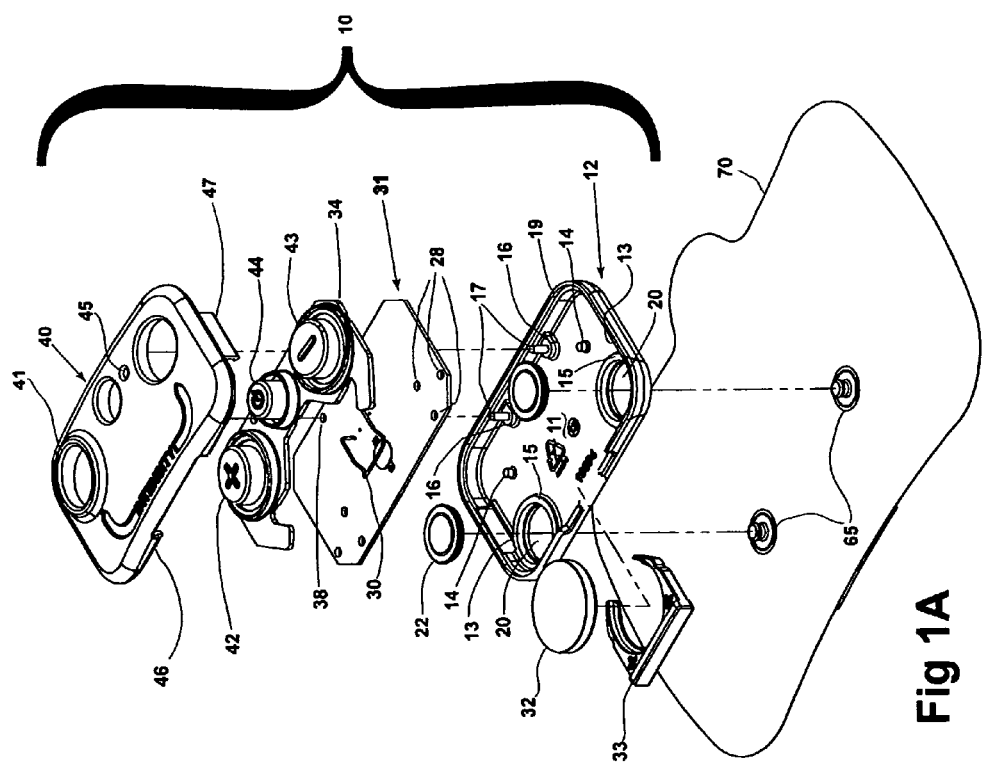

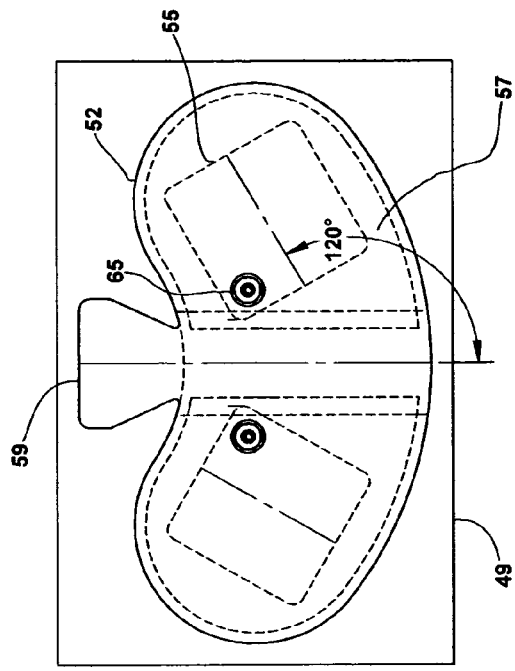
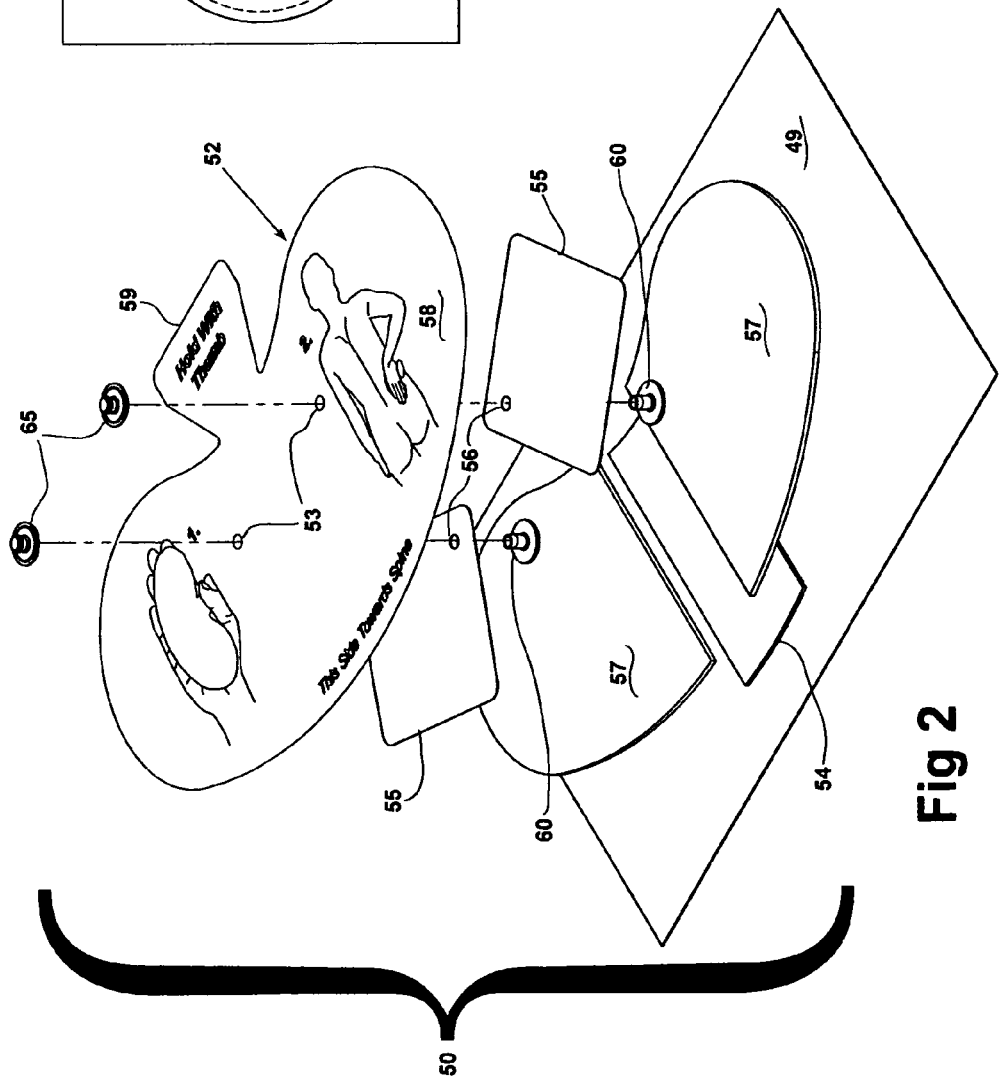

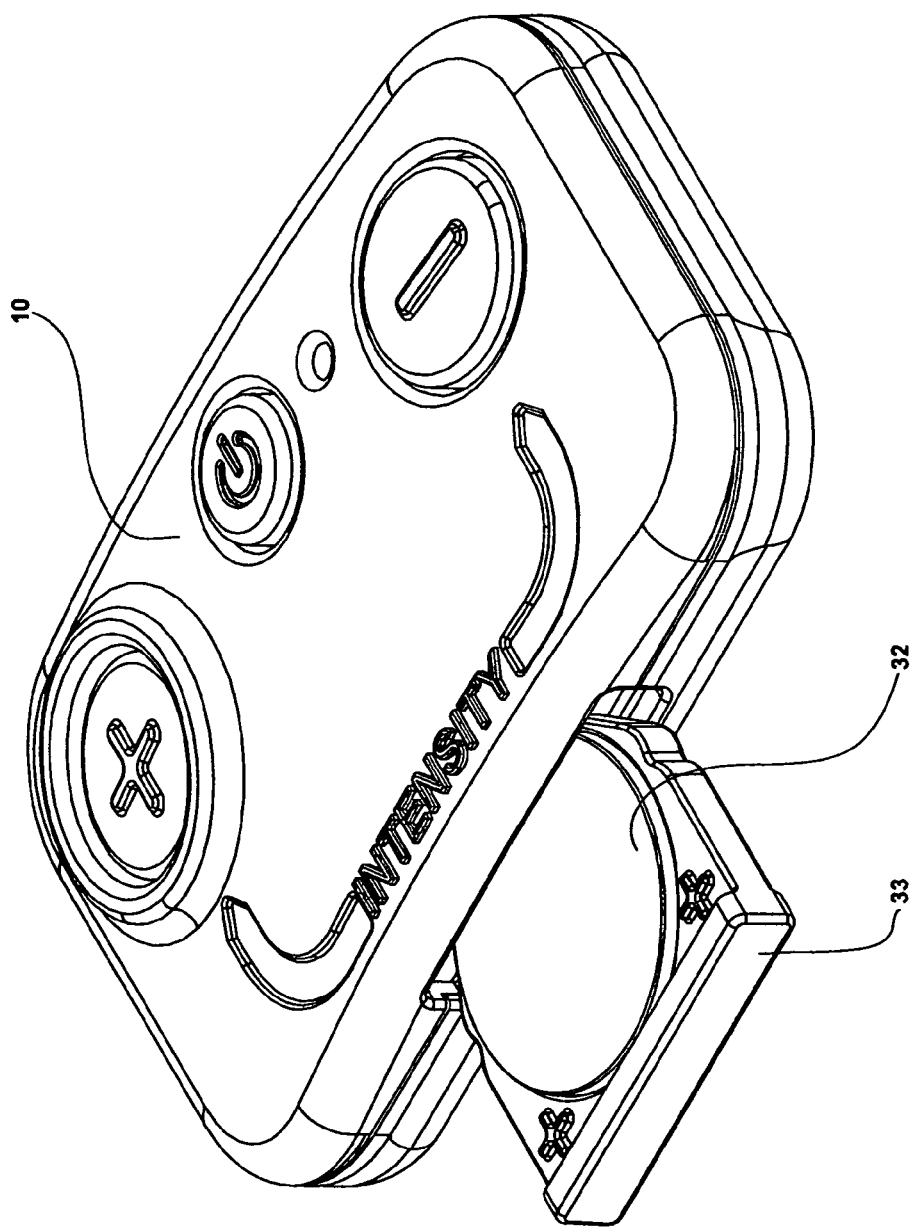

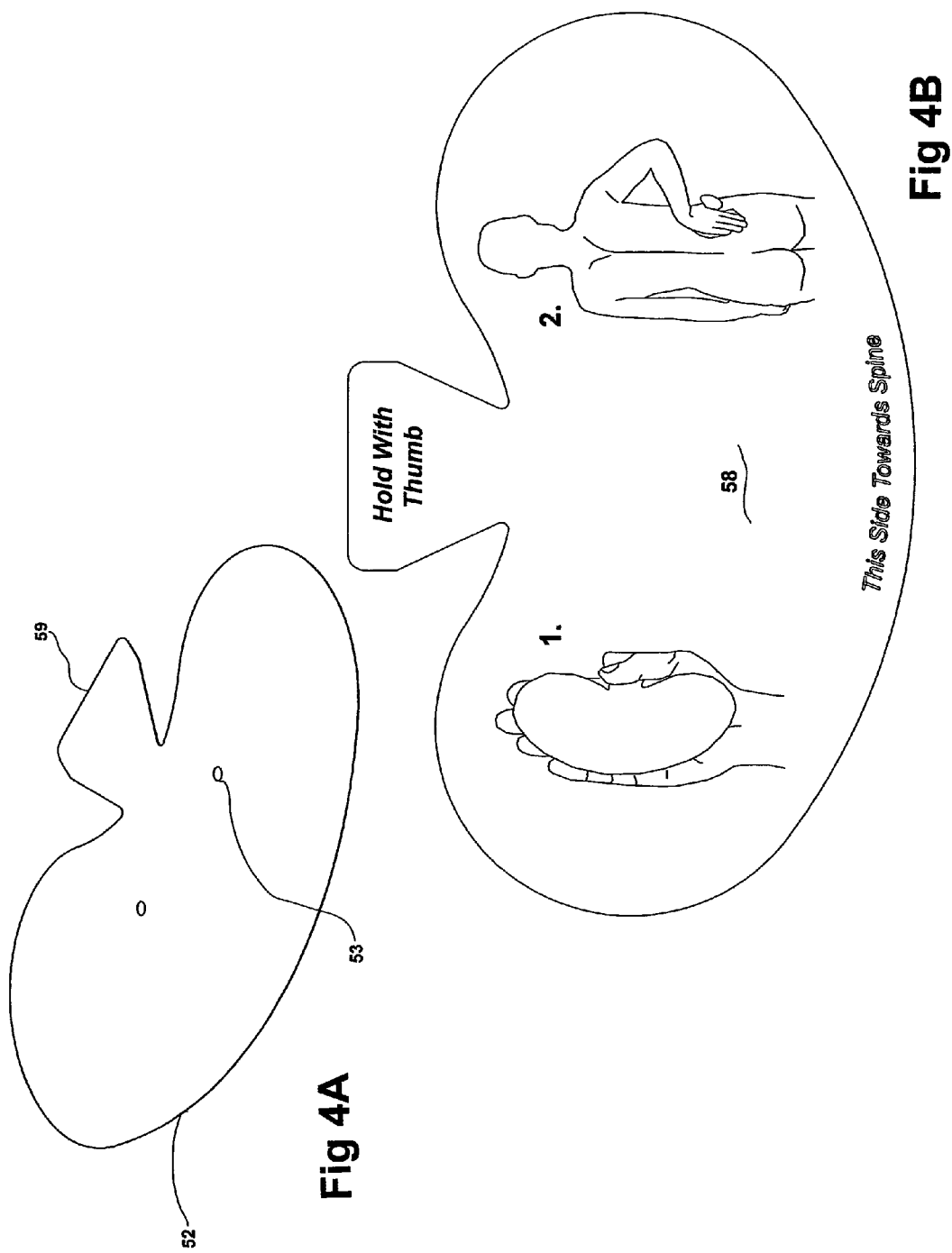

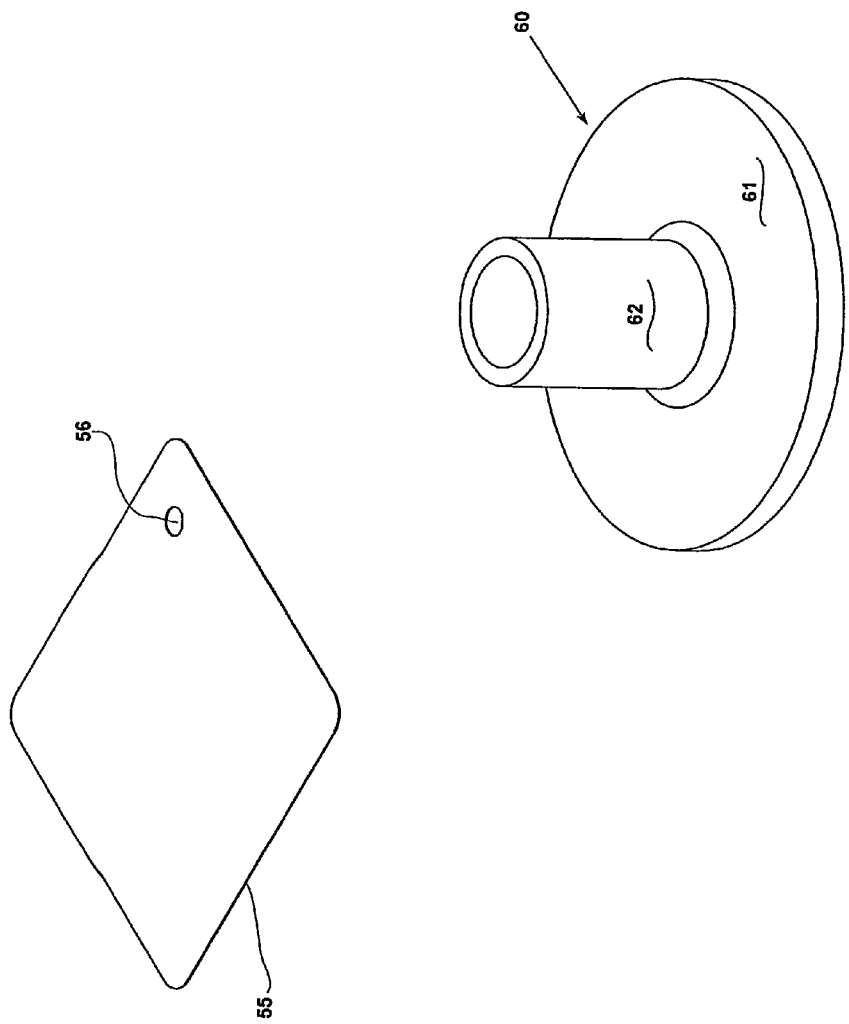

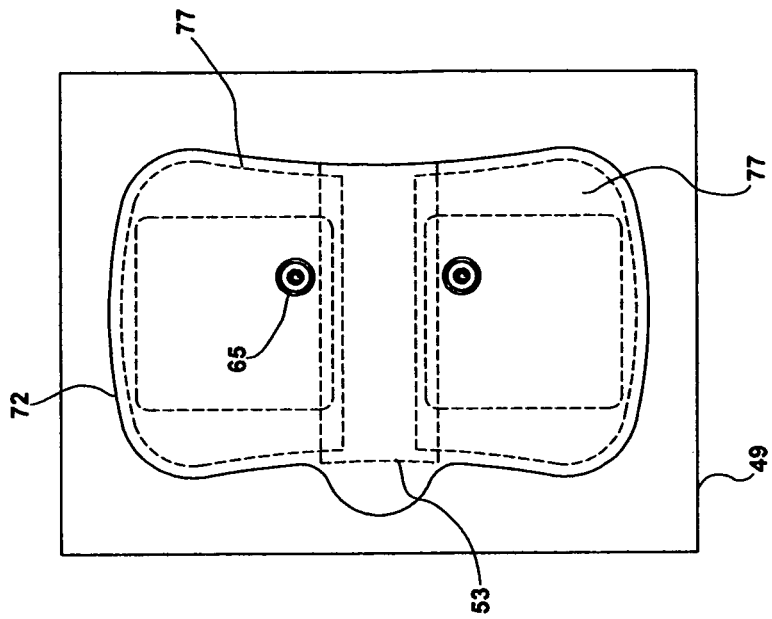
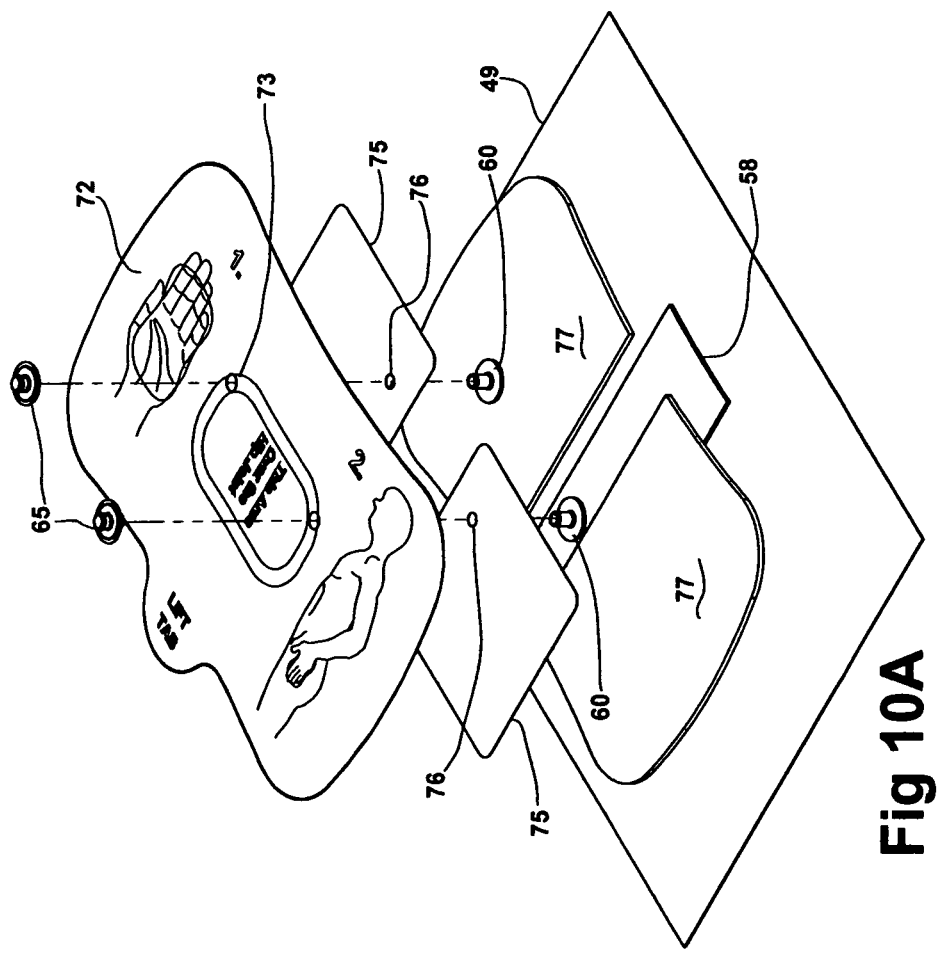
Fig 10B
Fig 10A

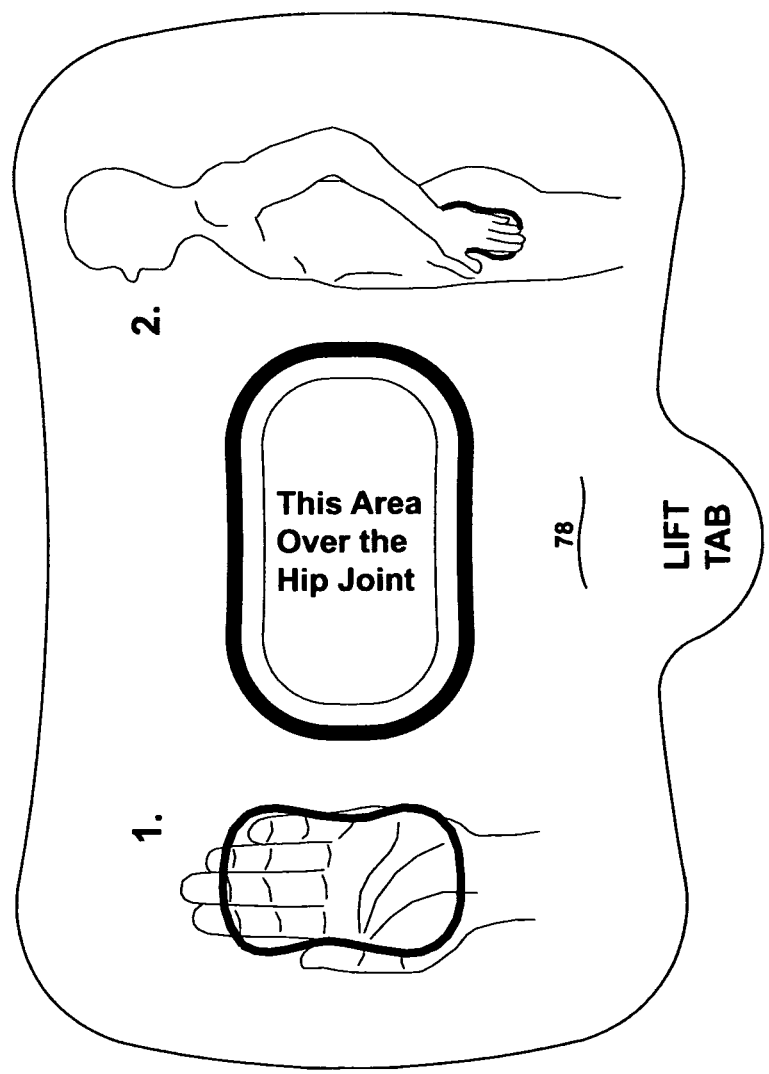

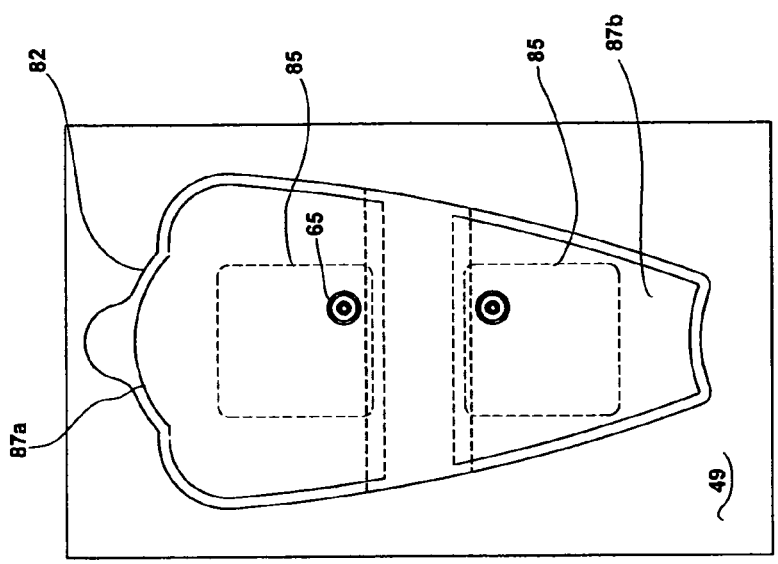
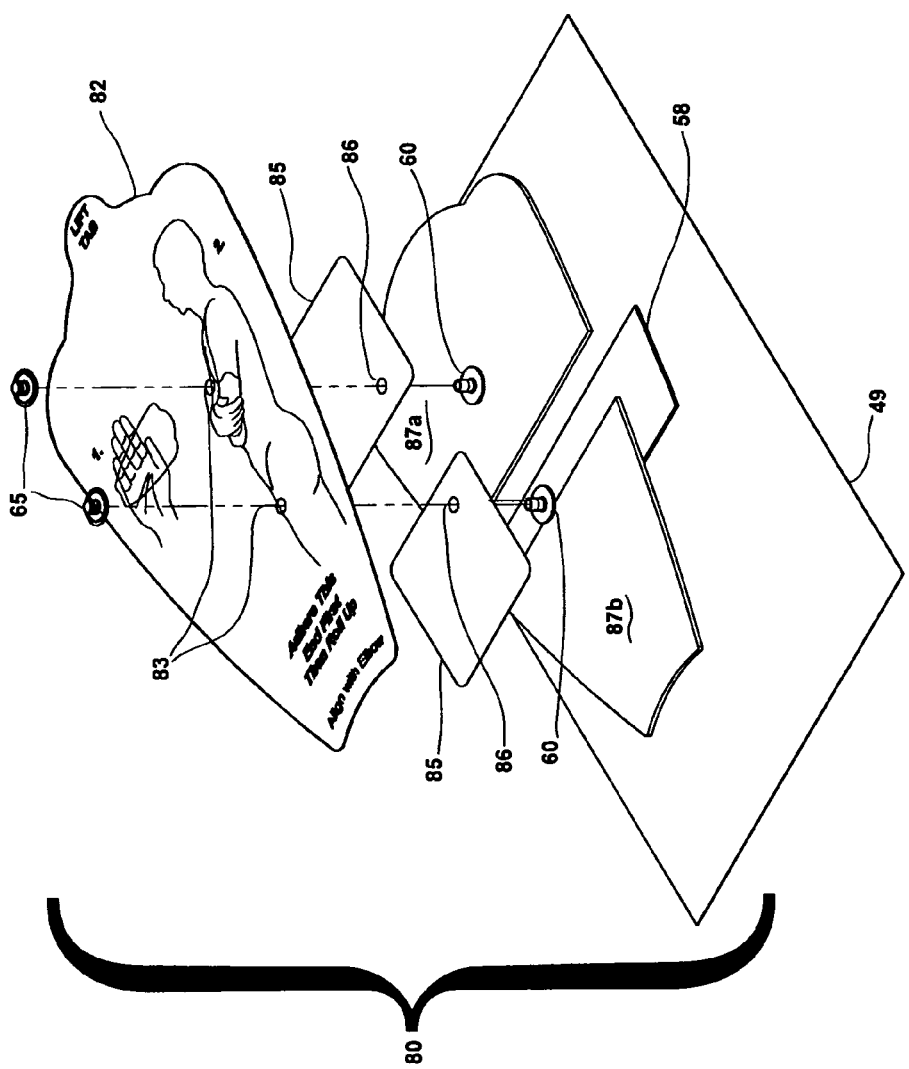
Fig 11B
Fig 11A

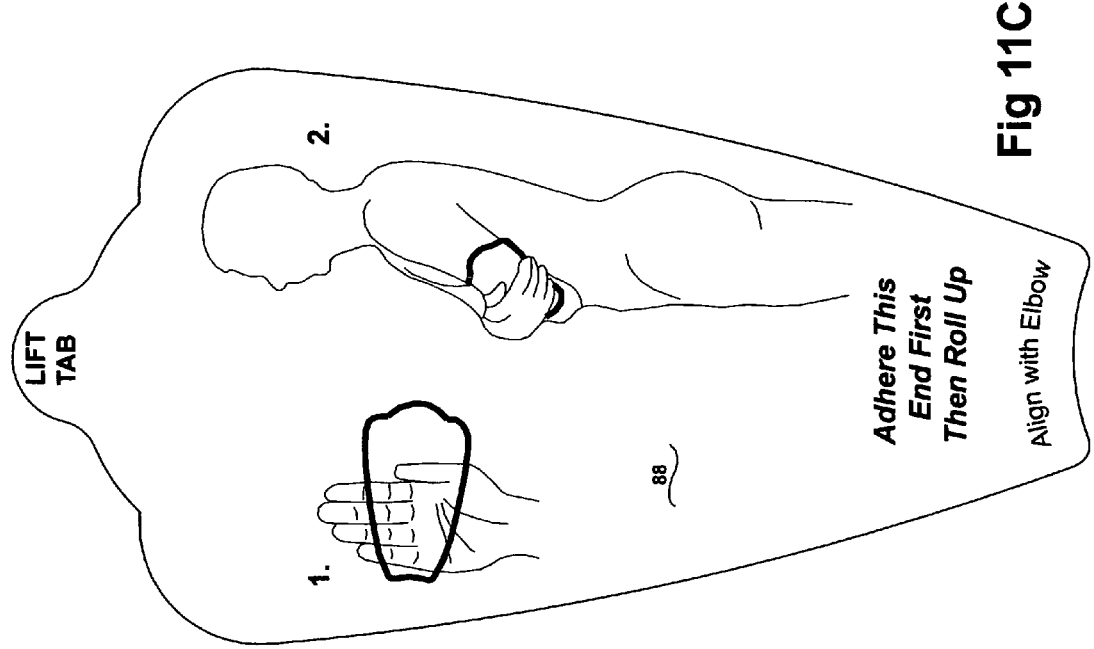

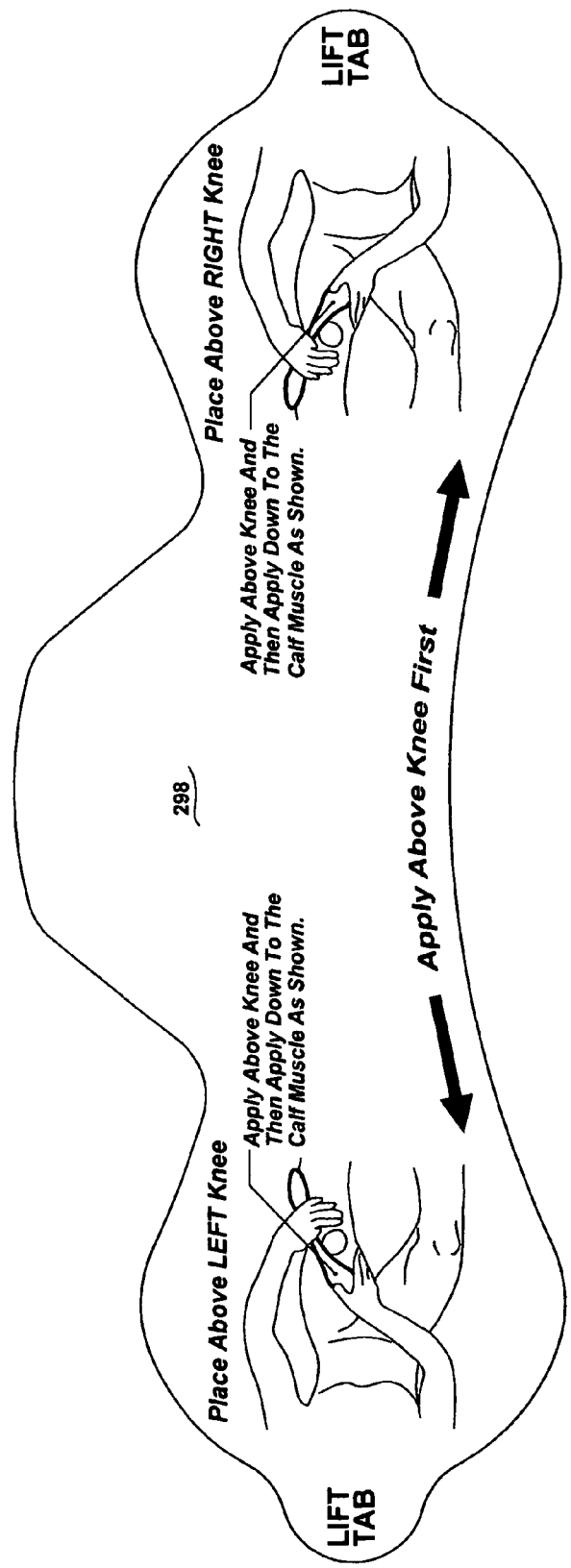

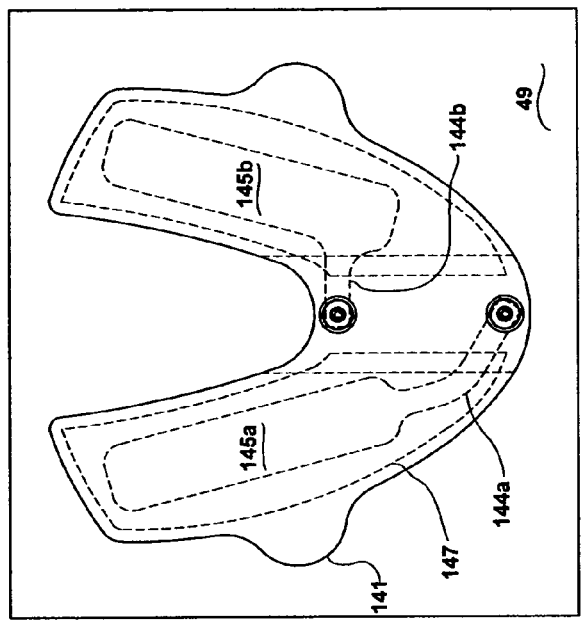
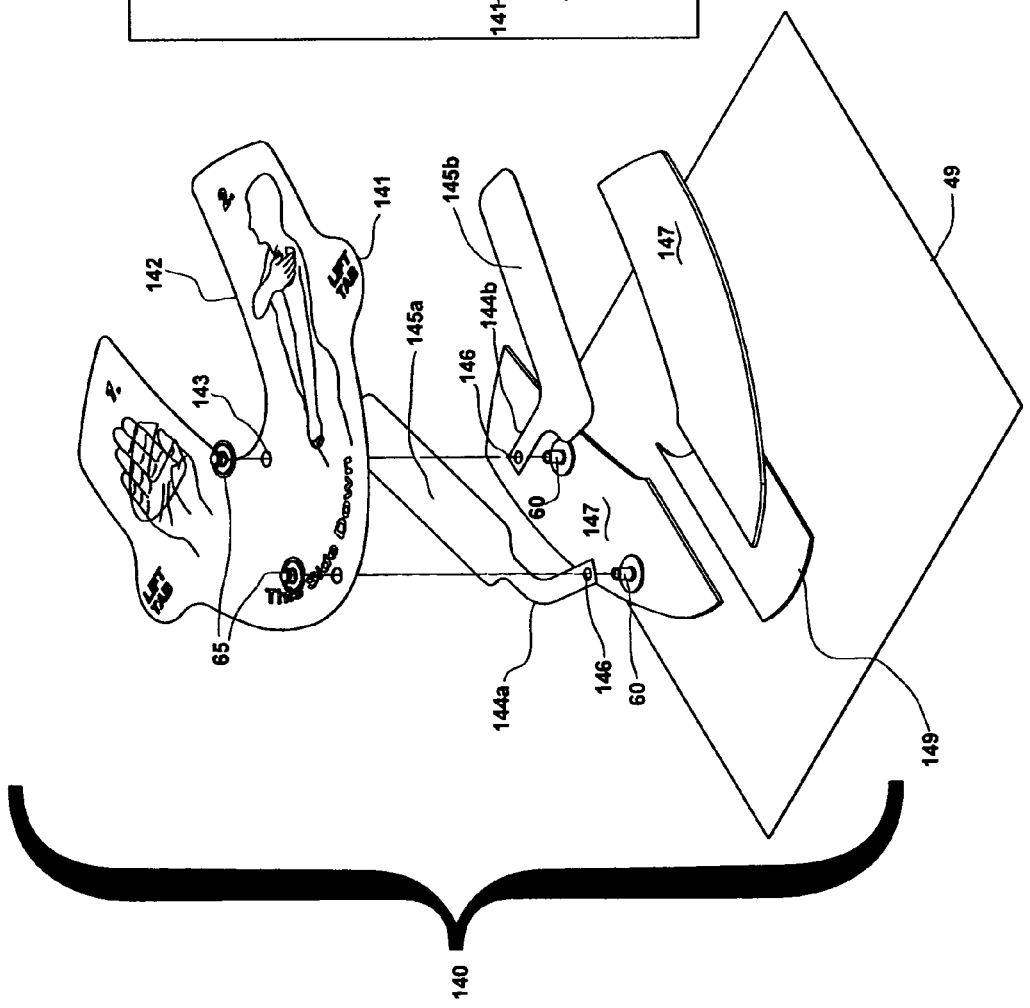
Fig 18A
Fig 18B

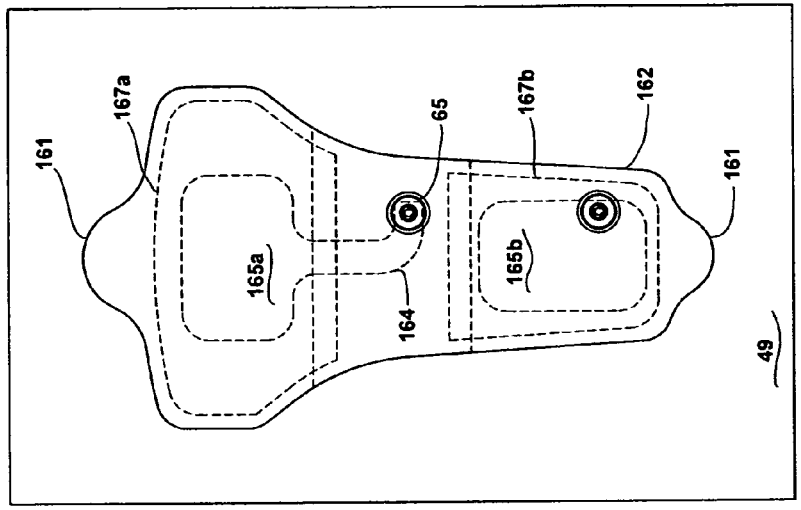
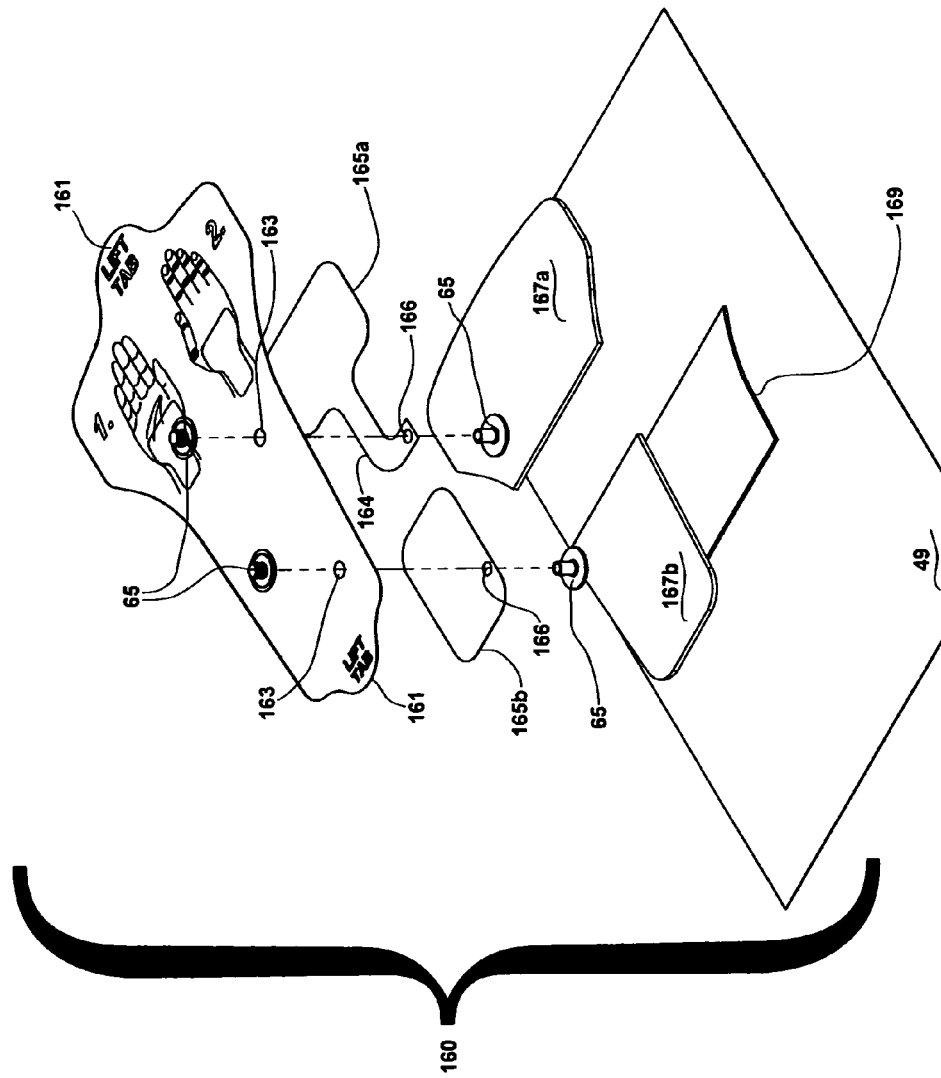
Fig 20B
Fig 20A

ELECTRO-STIMULATION SYSTEM

FIELD OF THE INVENTION

The present invention generally relates to an apparatus for applying electrical impulses to the body and is most particularly adapted to transcutaneous electrical neuro-stimulation (TENS) using a compact power and control assembly and improved gel pad electrodes.

BACKGROUND OF THE INVENTION

Gel pad electrodes are utilized in numerous medical diagnostic and treatment procedures to facilitate the application and measurement of electric impulses or signals in the body. For instance, conductive gel pads may be utilized to measure electrical signals when taking a patient's cardiogram. On the treatment side, the conductive gel pads are utilized not only in connection with TENS where electric current is applied to stimulate the nerves for therapeutic purposes, but also for Electrical Muscle Stimulation (EMS) or Neuromuscular Electrical Stimulation (NMES); Micro-current Electrotherapy or Bio-Electric Stimulation Therapy (BEST) delivering smaller amounts of current than the typical TENS application; iontophoresis transdermally delivering drugs through the use of electricity; and even in appropriate configurations for therapies such as bone growth stimulation. The presently described system is particularly adapted for TENS applications, and can be easily modified for NMES therapy, and with more substantial modifications to the power and control systems, to other related applications.

TENS is commonly used for pain management, and is most commonly administered by physical therapist or other medically trained personnel, and in conjunction with rehabilitation programs and possibly in conjunction with other pain management treatment. Most TENS devices are the size of a hand held calculator or television remote control apparatus, have a key pad and may have a small screen display, and are adapted to allow the operator to adjust the current intensity and wave form selected for treatment of the particular patient. Hand held devices may be battery operated, or even larger devices may be mounted to a mobile cart and provided with plugs and power converters to operate from an electrical socket. TENS may be utilized at high frequency or low frequency, and is applied in both palliative care and pain medicine. TENS is utilized for chronic pain as well as muscular-skeletal pain, labor pain, and period pain.

In operation, a TENS control device is connected by wires to conductive electrodes which are placed on the skin in the area of the pain. This allows a small, low-intensity electric charge to be passed across the area. In high frequency application, TENS is thought to work by selectively stimulating certain "non-pain" nerve fibers to send signals to the brain that block other nerve signals carrying pain messages. In low frequency application, TENS is thought to work by stimulating the production of endorphins, natural pain relieving opioid peptides. A TENS device may be utilized for extended periods, is usually utilized for 20 to 30 minutes of treatment at a time, and can be applied several times a day. While TENS is not addictive and seems have few side effects, especially compared to many pain medications, there are precautions that must be taken in placing the electrodes. For instance, electrodes should not be placed directly over the spinal column, patches to treat joint pain should generally not be placed directly over bony portions of the joints, and particular care must be taken in placing electrodes on the neck and chest.

In the typical TENS system, because there are wires connecting the control device to the gel electrode pads, care must be taken to connect to the electrode pads correctly and the wearer may be restricted in movements because wires could become disconnected, tangled, or catch on objects. Consequently, the application of TENS treatment is presently most effectively administered by medically trained personnel in a therapeutic or treatment setting. The prior art does not disclose a simple apparatus to allow a patient to apply electric stimulation to a variety of patient selected locations. Neither does the prior art disclose apparatus that is easily wearable by a patient in a fashion that conceals the TENS apparatus with ordinary clothing and that is easy for the patient to operate.

SUMMARY OF THE INVENTION

The present invention is an electro-stimulation apparatus that is preferably provided in a very compact form with simplified operational controls. The control and power assembly may be provided in a module only about 1" by 2" in size and only about 0.3 inches in thickness. Furthermore, the control and power assembly may be designed with snap elements to connect directly with mating snap elements protruding from gel pads. In this fashion, the entire thickness of the combined pad and control apparatus is less than 0.5 inches, there are no exposed wires, and the apparatus can be worn and concealed under many types of clothing. Furthermore, the gel electrode pads are provided in a variety of shapes and each shape is imprinted with placement instructions or placement illustrations to facilitate use of the TENS apparatus by a patient without medical training. Some or all of these objectives may be accomplished by various embodiments of the invention.

BRIEF DESCRIPTION OF THE DRAWINGS

For more complete understanding of the various elements of the improved electro-stimulation system, reference is now made to the following descriptions taken in conjunction with the accompanying drawings in which:

FIG. 1A is an exploded perspective view of an exemplary electro-stimulation system according to the invention with a gel electrode pad design shaped for application over the hip joint area.

FIG. 1B is a reverse angle view of the underside of the case top shown in FIG. 1A.

FIG. 1C is a side plan sectional view of a female snap shown in FIG. 1A.

FIG. 1D is a bottom plan view of the female snap shown in FIG. 1C.

FIG. 2 is an exploded perspective view of a gel electrode patch shaped for application to a patient's back;

FIG. 3A is a top plan view of the patch of FIG. 2 showing the positioning of patch components in phantom;

FIG. 3C is a perspective view of the power and control case of the system of FIG. 3B opened for battery access.

FIG. 4A is a perspective view of the top sheet of the pad of FIG. 2.

FIG. 4B is a plan view of the art work imprinted on the top sheet illustrated in FIG. 4A;

FIG. 5 is a perspective view of one of the conductive pads in the gel electrode pad of FIG. 2;

FIG. 6 is a perspective view of an anchor post for the male snap in the gel electrode pad of FIG. 2.

FIG. 10A is an exploded perspective view of a gel electrode patch assembly designed for application to a hip joint;

FIG. 10B is a top plan view of the patch of FIG. 10A illustrating the location of components within the patch in phantom;

FIG. 10C is a top plan illustration of the art work imprinted upon the top sheet of the gel electrode pad of FIG. 10A.

FIG. 11A is an exploded perspective view of a gel electrode patch configured for use on a patient's upper arm;

FIG. 11b is a top plan view of the patch of FIG. 11A showing the location of components of the patch in phantom;

FIG. 11C is a top plan view of the art work imprinted upon the top sheet of the patch of FIG. 11A;

FIG. 14C is a top plan view of the art work imprinted upon the top sheet of the patch of FIG. 14A.

FIG. 18A is an exploded perspective view of a gel electrode patch configured for use about the shoulder of a patient;

FIG. 18B is a top plan view of the patch of FIG. 18A showing in phantom the location of the patch components;

FIG. 20A is an exploded perspective view of a gel electrode patch configured for use on the wrist and hand of a patient;

FIG. 20B is a top plan view of the patch of FIG. 20A showing in phantom the location of the patch components;

DETAILED DESCRIPTION OF THE INVENTION

Figure 3B:
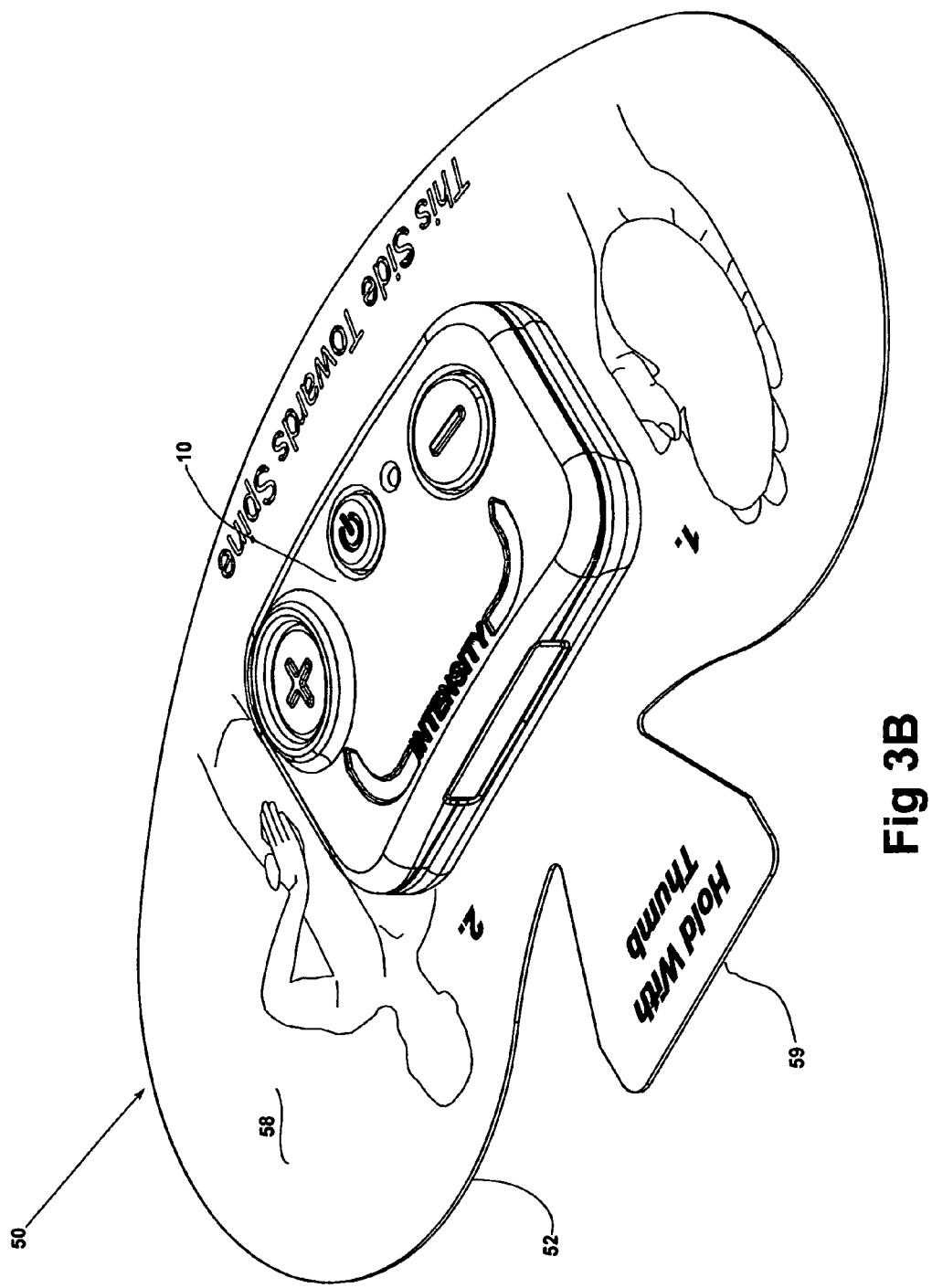
FIG. 3B is a perspective view of the electro-stimulation system with the gel electrode patch of FIG. 2.

Turning now to the drawings, in which like numerals indicate like elements throughout the several views of an electro-stimulation system, the exemplary components of such a system are illustrated in FIG. 1A. A power and control case 10 is shown in exploded form with the principal elements consisting of the case top panel 40, the back panel 12, and circuit board 31. The size of the case 10, is preferably only about 1 inch by 2 inches and little more than a quarter inch in thickness. As the size of the electronics are reduced, the thickness of the case 10 can also be reduced. The circuit board 31 is of conventional design and its principal features include battery clip 30 to contact with battery 32 mounted in slidingly removable battery housing 33. The battery 32 provides power for the electro-stimulation system and its controls. Apertures 38 in the circuit board 31 are designed to receive positioning posts 17. Switches are preferably encased in silicon keypad 34 to operate in connection with buttons 42, 43, 44. These buttons, in turn, are received through openings on the case top panel 40, and an LED provides a visible light signal through opening 45 when the electro-stimulation system is operating. Additional circuitry on circuit board 31 is of conventional nature to produce one or more desired wave forms, to permit the power intensity to be adjusted, and to permit the system to be turned off and on.

Emerging through openings on the surface of case top panel 40, are three illustrated control buttons, namely, an intensity decrease button 43, an intensity increase button 42, and an activation or on/off button 44. The light signal visible through opening 45 indicates that the electro-stimulation system is operating. Surrounding the increased intensity button 42 is a raised flange 41. The flange 41 is a safeguard that protects against the inadvertent depression of button 42 which would cause a corresponding increase of electrical intensity. Additional features of case top panel 40 include a downward facing recessed lip 46, and extending tabs 47 at either side of the panel. The circuit board 31 is aligned beneath the case top panel 40 so that depression of on/off button 44 will activate a corresponding switch and transmit the appropriate signal to the circuit board. Similarly, depressing the intensity increase button 42 or depressing the intensity decrease button 43 will activate corresponding switches to signal the instruction to the circuit board. These simplified user controls allow for manual operation of the electro-stimulation system without the need for professional training. When the system is turned on, a timer circuit is activated and the system will operate for a predetermined interval, typically between 20 and 30 minutes. If additional electro-stimulation therapy is desired, the user must reactivate the system by depressing the on/off button 44. It can be appreciated that one or more additional control buttons may be added to permit the user to easily select from a variety of wave forms, or to select from high-frequency or low-frequency therapy.

The exemplary back panel 12 has a generally rectangular back surface 11 and a raised perimeter with an upwardly extending lip 19 for a secure fit minimizing the possibility of water ingress. It can be seen that the downwardly extending recessed lip 46 of the case top panel 40 will fit within the upwardly extending lip 19. In addition, the back panel 12 preferably has a plurality of short posts 14 that will support the circuit board 31 in an intermediate position between the back panel 12 and case top panel 40. A plurality of larger posts 16 also extend upward from the rectangular back surface 11, and then extend inward presenting a lateral surface and then further upward in a narrower post extension 17. Apertures 38 on circuit board 31 receive these narrow upwardly extending post extensions 18 and the circuit board can rest on the lateral surfaces.

At either side of back panel 12 is a slot 13 to receive extending tabs 47 of the case top panel 40. The tabs 47 may flex sufficiently to allow the locking and unlocking of the case top panel 40 and back panel 12 when the extending tabs 47 are engaged and disengaged from back panel slots 13. This allows the case to be assembled without screws or adhesives, although alternative or permanent fastening of the case is possible.

Finally, back panel 12 has two openings 20 extending downward through the rectangular back surface 11. Openings 20 are surrounded by upwardly extending arcuate walls 15. Female snaps 22, shown in detail in FIGS. 1C and 1D rest with their outer flanges 25 on raised walls 15. Raised back surface 23 of snaps 22 interfaces with electrical connections on circuit board 31. When the power and control case 10 is assembled downwardly facing recess 26 of snaps 22 are exposed. The downwardly facing recesses 26 and interior flanges 27 serve as electrode connections.

Figure 7A:
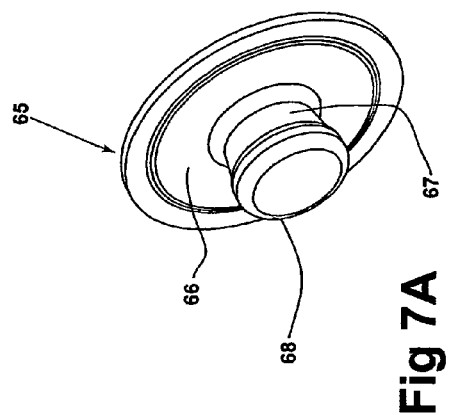
FIG. 7A is a perspective view of the male snap that is affixed to the anchor post of FIG. 6 in the construction of the gel electrode pad of FIG. 2.
Figure 7B:
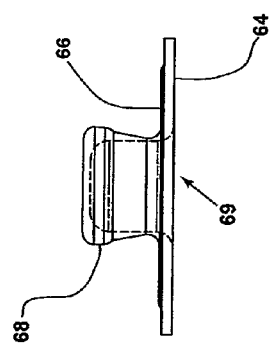
FIG. 7B is a side plan view of the male snap of FIG. 7A.

As can be seen from the exemplary hip gel electrode pad 70 in FIG. 1A, a pair of male snaps 65 extend upward from nonconductive top surface of the pad 70. These snaps 65 are shown in greater detail in FIGS. 7A and 7B. It can be seen that post 67 extends upward from the circular body 66 of the male snap 65 to an expanded plug section 68 which is adapted to be received in the downwardly facing cavities 26 of the female snaps 22 mounted within the power and control case 10. The plug section 68, post 67 and exposed portion of body 66, serve as electrode leads.

Turning then to FIGS. 2, 3 and 4A and 4B, the construction of an exemplary gel electrode pad 50 designed for use on a user's back is shown in detail. The pad 50 is formed of six significant components. These components are the male snaps 65 and their corresponding mounting posts 60, a backing sheet 49, conductive gel portions 57, conductive pads 55, a fabric insulator sheet 54 and a nonconductive top sheet 52. As illustrated in FIG. 6, each anchor post 60 has an upward facing flange section 61 and an upward extended post 62. The posts 62 pass through apertures 56 in conductive pads 55. The posts 62 also extend upward through apertures 53 in the nonconductive top sheet 52 and are received within the openings 69, shown in FIG. 7B, of the male snaps 65. Conductive gel portions 57 are formed from conductive and tacky hydrogel material and also help hold the conductive pads 55 in place against nonconductive top sheet 52. The conductive gel portions 57 are spaced apart and may be advantageously separated by a fabric insulator sheet 58 to insure the current flow is primarily across the patient's skin.

For therapeutic use, the backing sheet 49 is removed from the gel electrode 50, exposing a tacky surface of the conductive gel sections 57 which will adhere to a patient's skin. In the particular embodiment 50, the top sheet 52 is generally bean or kidney-shaped, but also has a tab 59 on which no tacky conductive gel is placed. As will be discussed later, this tab is used by a patient in positioning the pad for use and in removing the pad after use. In FIG. 3A, the relative locations of the conductive gel sections 57 and conductive pads 55 are illustrated. Specifically, there is a space of about 0.8 inches between the two conductive gel sections separated by a fabric insulator 5B. The closest portions of the conductive pads 55 are approximately 1 inch apart and the male snaps 65 are 1.7 inches apart. Generally, a spacing of 0.6 to 2 inches is preferred to provide the most effective TENS treatments. The 1.7 inch spacing between the pair of male snaps 65 is the distance between the female snaps 22 mounted in the exemplary power and control module 10. The 1.7 inch spacing could be adjusted to between about 0.8 and 2.0 inches without compromising the effectiveness of the system.

FIG. 3B illustrates the power and control case 10 attached to the gel electrode 50. FIG. 3C shows the power and control case in isolation with the battery housing pulled out to permit access to the battery 32.

FIG. 4B shows the instructions 58 that are preferably printed or otherwise placed on the top sheet 52 to provide written and illustrative instructions to the user. In the case of the illustrated back gel electrode pad 50, the tab 59 is intended to be grasped by the user's thumb and then the opposite rounded side of the pad is placed alongside the user's spine. Heretofore, it has been very difficult to provide gel electrodes that could be utilized by a patient for self-treatment on their back, and most particularly for treatment without the necessity of wires connecting electrodes on the gel pad to a physically separate power and control module.

Figure 9:
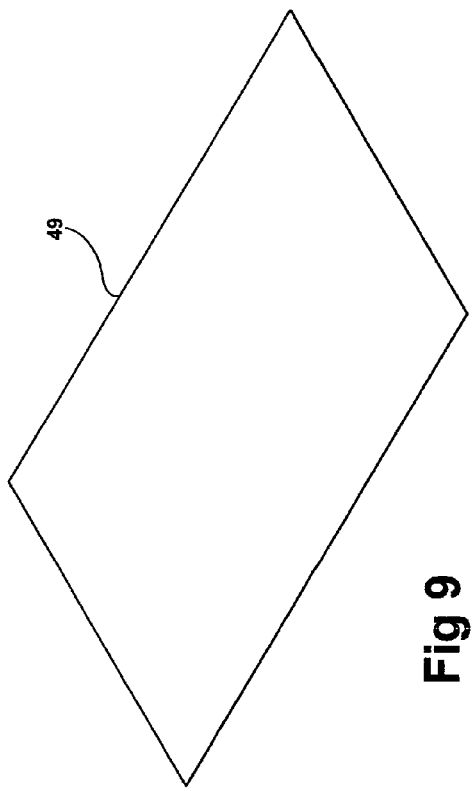
FIG. 9 is a perspective view of the backing sheet for the gel electrode pad of FIG. 2.
Figure 8:
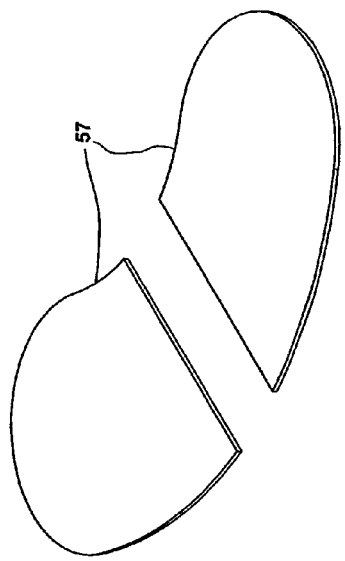
FIG. 8 is a perspective view of the conductive gel portions of the gel electrode pad of FIG. 2.

FIG. 5 shows an exemplary conductive pad 55 and its aperture 56 in isolation and FIG. 8 shows the conductive gel sections 57 for the back gel electrode pad 50. The conductive pads 55 are preferably made of a flexible carbon construction and may be coated with a silver compound for improved conductivity, however, alternative conductive constructions of other suitable materials may be used. FIG. 9 illustrates an exemplary backing sheet 49 in isolation. The backing sheet 49 is preferably a thin poly-coated paper release liner, but may be made from many materials that are suitable to protect the gel from drying while not in use.

Figure 10D:
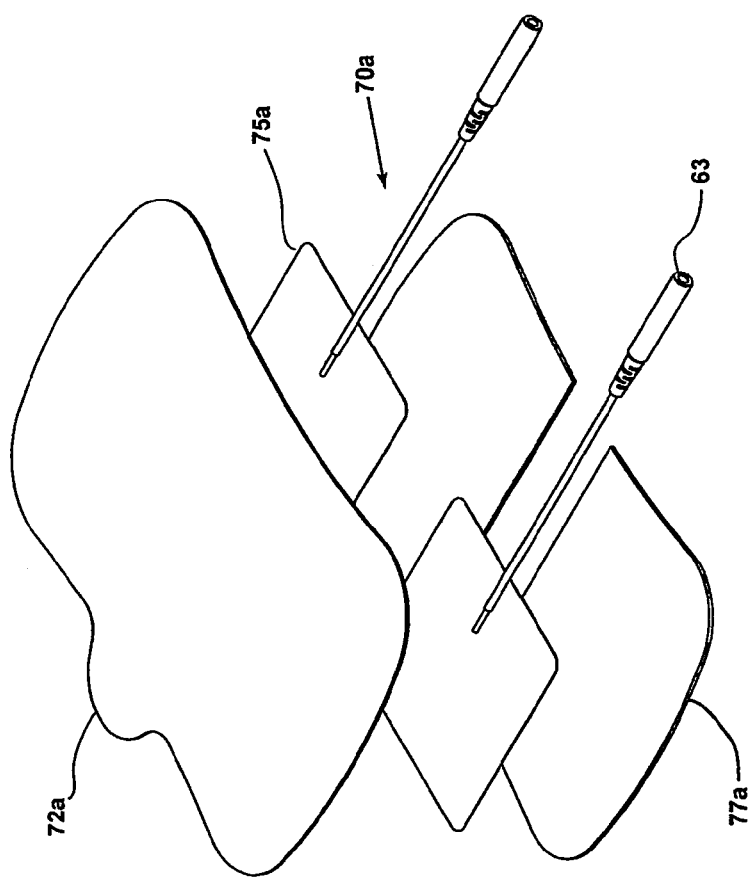
FIG. 10D is an exploded perspective view of a gel electrode patch configured for application to a patient's hip joint with conventional wire electrode attachment connections.

FIGS. 10A through 10D shown two exemplary hip gel electrode pads 70, 70a. In FIG. 10A, the male snaps 65 can be seen above top sheet 72, conductive pads 75, anchor posts 60, conductive gel segments 77 and backing sheet 49. As with the back gel electrode pad 50, the upward extending posts 62 of anchor posts 60 extend through apertures 76 of conductive pads 75 and apertures 73 in top sheet 72 to be received within the recesses 69 on the rear of male snaps 65. The plan view of FIG. 10B shows the spacing between conductive gel section 77 at 0.75 inches, between conductive pads 75, a slightly greater distance, and between male snaps 65 at 1.7 inches. Fabric insulation 58 is also between the conductive pads 55. Although the 1.7 inch spacing between snaps 65 is required to meet the corresponding spacing of the exemplary power and control case 10 illustrated in FIG. 1, other dimensions of the gel electrode may be varied somewhat and in particular, the overall patch size may be generally decreased for use by a smaller patient or for treatment of more localized pain sensation.

FIG. 10C illustrates the art work 78 that is preferably printed on top sheet 72 to provide graphic and textual information to the user on the application of the hip electrode 70.

FIG. 10D shows an alternative hip electrode 70a with conductive pads 75a connected to traditional wire electrodes 63 and with the conductive gel sections 77a holding the conductive pads 75a against the top sheet 72a. This more conventional pad design is intended for use with conventional power and control systems, and particularly those operated by medically trained personnel.

FIGS. 11A through 11C illustrate an upper arm gel electrode patch 80, again with backing sheet 49, fabric insulation 58, conductive gel sections 87a, 87b, anchor posts 60 extending upward through openings 86 and 83 in conductive pads 85 and top sheet 82 respectively, until being received within back cavity 69 on male snap 65. A top plan view of FIG. 11B illustrates the 0.80 inch spacing between conductive gel sections 87a, 87b, and the 1.7 inch spacing between male snaps 65. FIG. 11C illustrates the art work 88 that is preferably printed on top sheet 82 to graphically and textually educate the user on the proper application of the arm electrode 80.

Figure 12B:
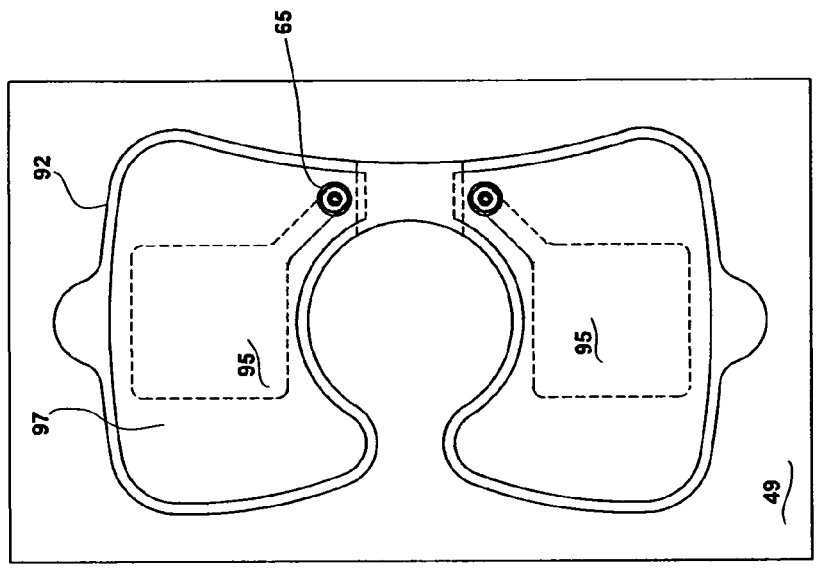
FIG. 12B is a top plan view of the patch of FIG. 12A showing in phantom the location of components of the patch.
Figure 12A:
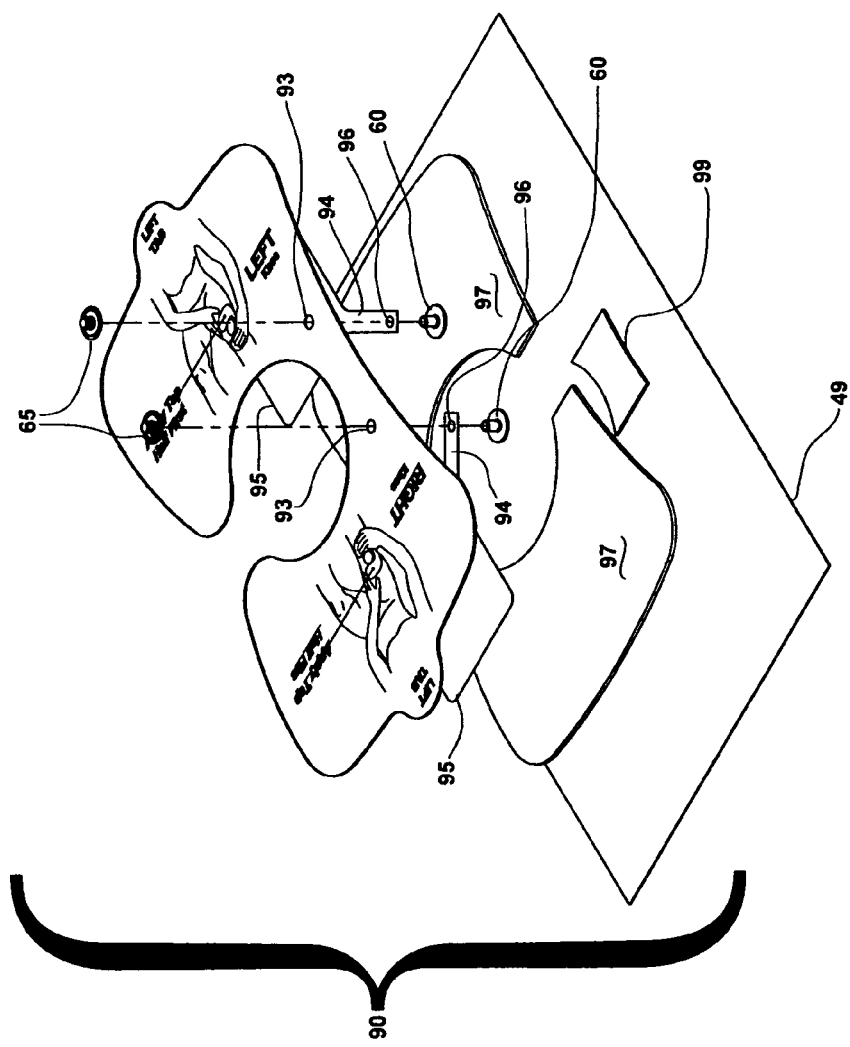
FIG. 12A is an exploded perspective view of a gel electrode patch configured for use about a patient's knee.
Figure 12C:
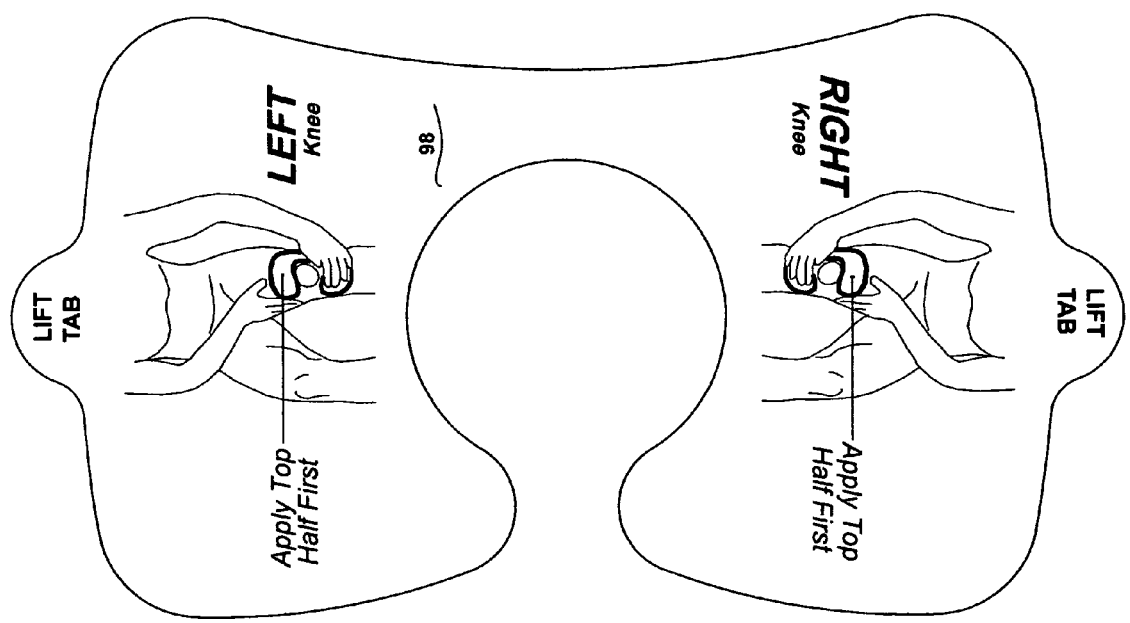
FIG. 12C is a top plan view of the art work imprinted on the top sheet of the patch of FIG. 12A.

FIGS. 12A through 12C illustrate a small knee gel electrode 90. The construction of electrode 90 is similar with backing sheet 49, fabric insulation 99, gel sections 97, anchor posts 60 with upwardly extending posts 62 passing through apertures 96 in conductive pads 95 and through apertures 93 in upper sheet 92 until received within the rear cavity 69 on male snap 65. The shape of the conductive pads 95 is modified to provide an extension 94 so that the spacing between snaps 65 can remain at 1.7 inches, corresponding to the fixed female snap 22 portions in the power and control module 10, while the overall shape of the electrode is modified to provide an opening around the wearer's knee so that therapy is not applied directly on the joint, but instead on the surrounding tissue. FIG. 12C illustrates the art work 98 showing in text and graphics, the appropriate use of the electrode 90.

Figure 13B:
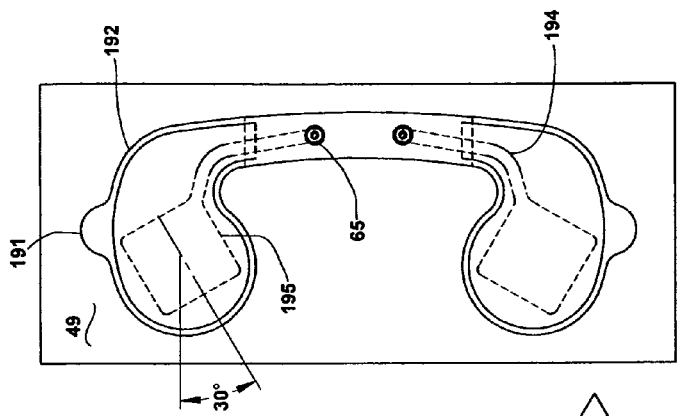
FIG. 13B is a top plan view of the patch of FIG. 13A showing in phantom the location of the patch components.
Figure 13A:
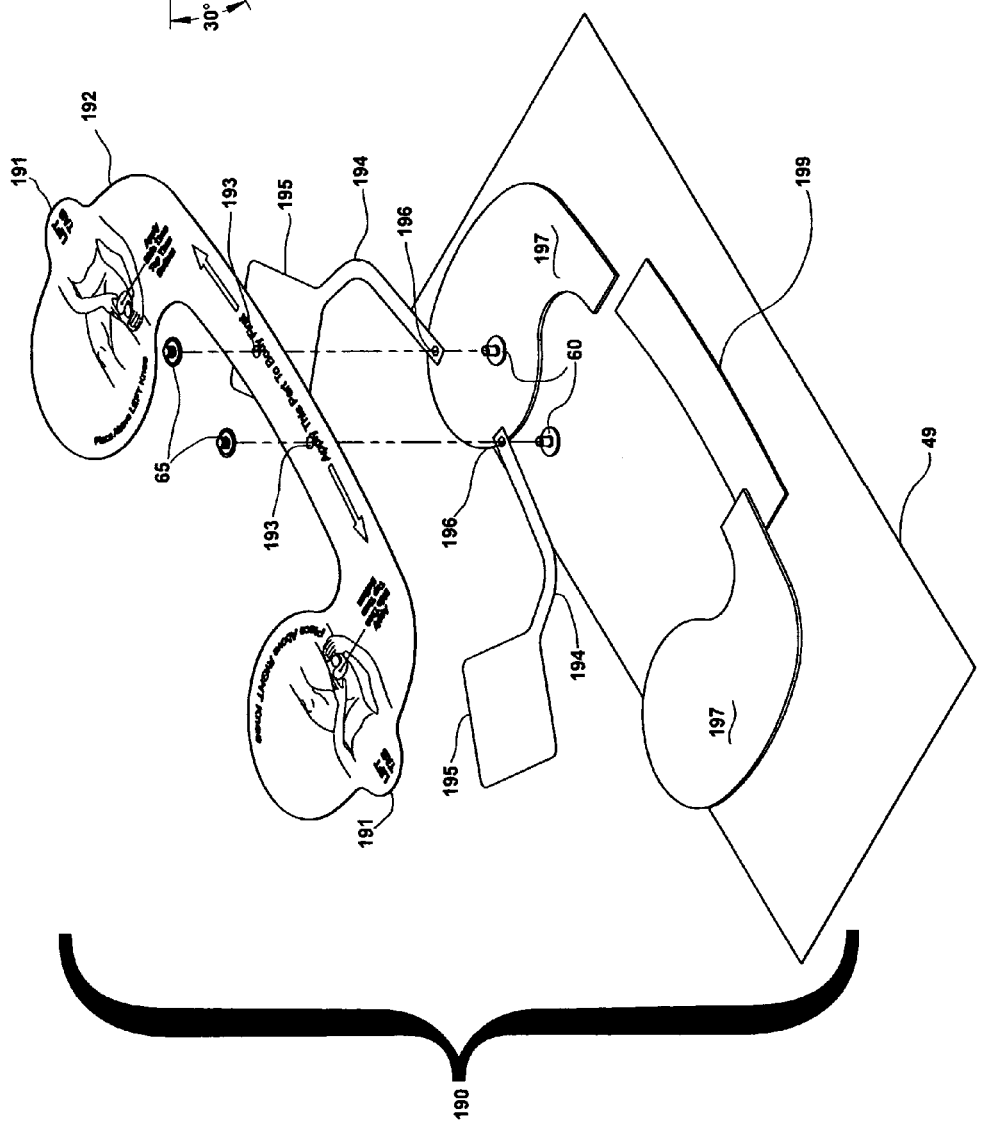
FIG. 13A is an exploded perspective view of a gel electrode patch configured for use about the knee of a large patient.
Figure 13C:
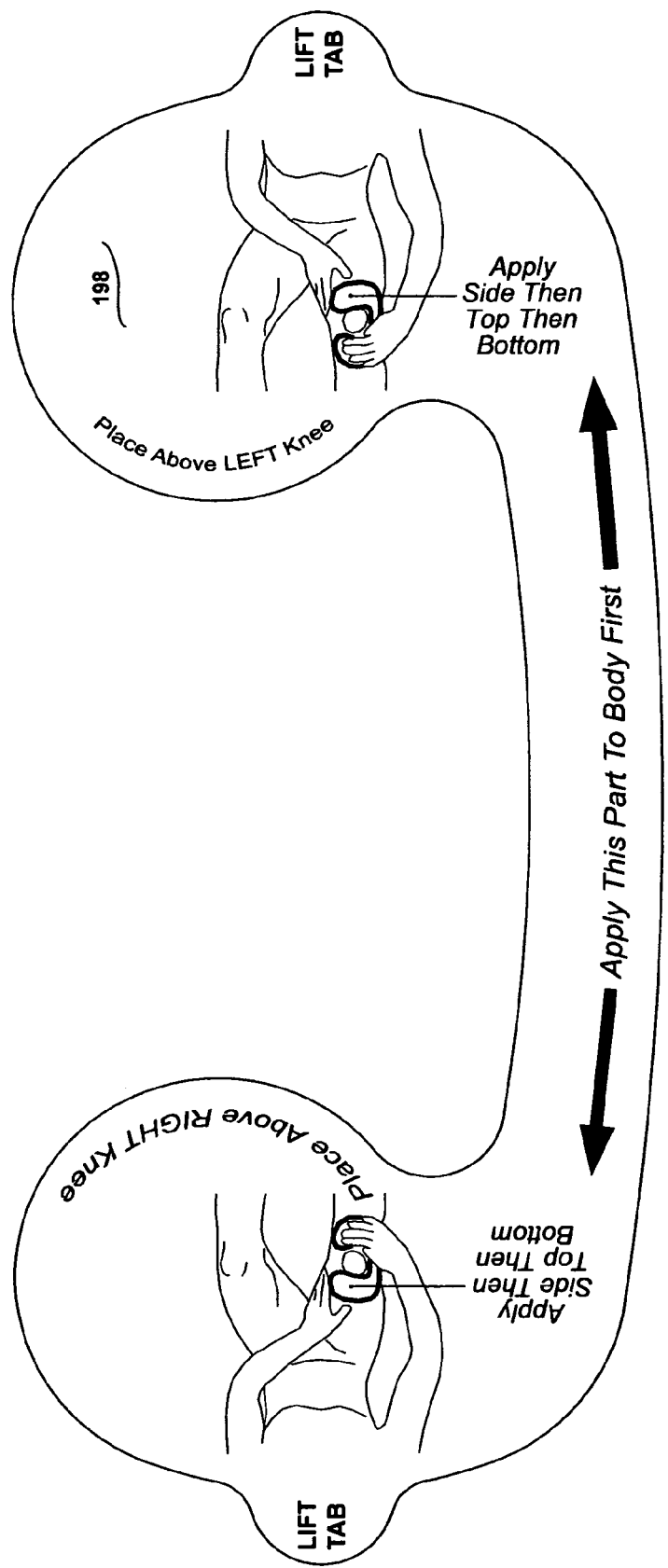
FIG. 13C is a top plan view of the art work imprinted upon the top sheet of the patch of FIG. 13A.

FIGS. 13A-C illustrate a second knee gel electrode patch 190 but one designed for a large knee. The structure of the patch 190 is again similar with back sheet 49, fabric insulation 199, conductive gel sections 197, anchor posts 60 with upward extending post sections 62 passing through apertures 196 in conductive pads 195 and through apertures 193 in top sheet 192 until received in back recesses 69 of snaps 65. Top sheet 192 has lift tabs 191 at either end to facilitate placement and removal. As shown in the plan view of FIG. 13B, spacing between the gel sections 197 is one inch and the conductive pads 195 have lengthy leg sections 194 to permit the spacing of snap 65 to remain at 1.7 inches. Finally, the printed art work 198 shown in FIG. 13C provides text and graphical information to advise the user upon the proper application of the electrode 190.

Figure 14A:
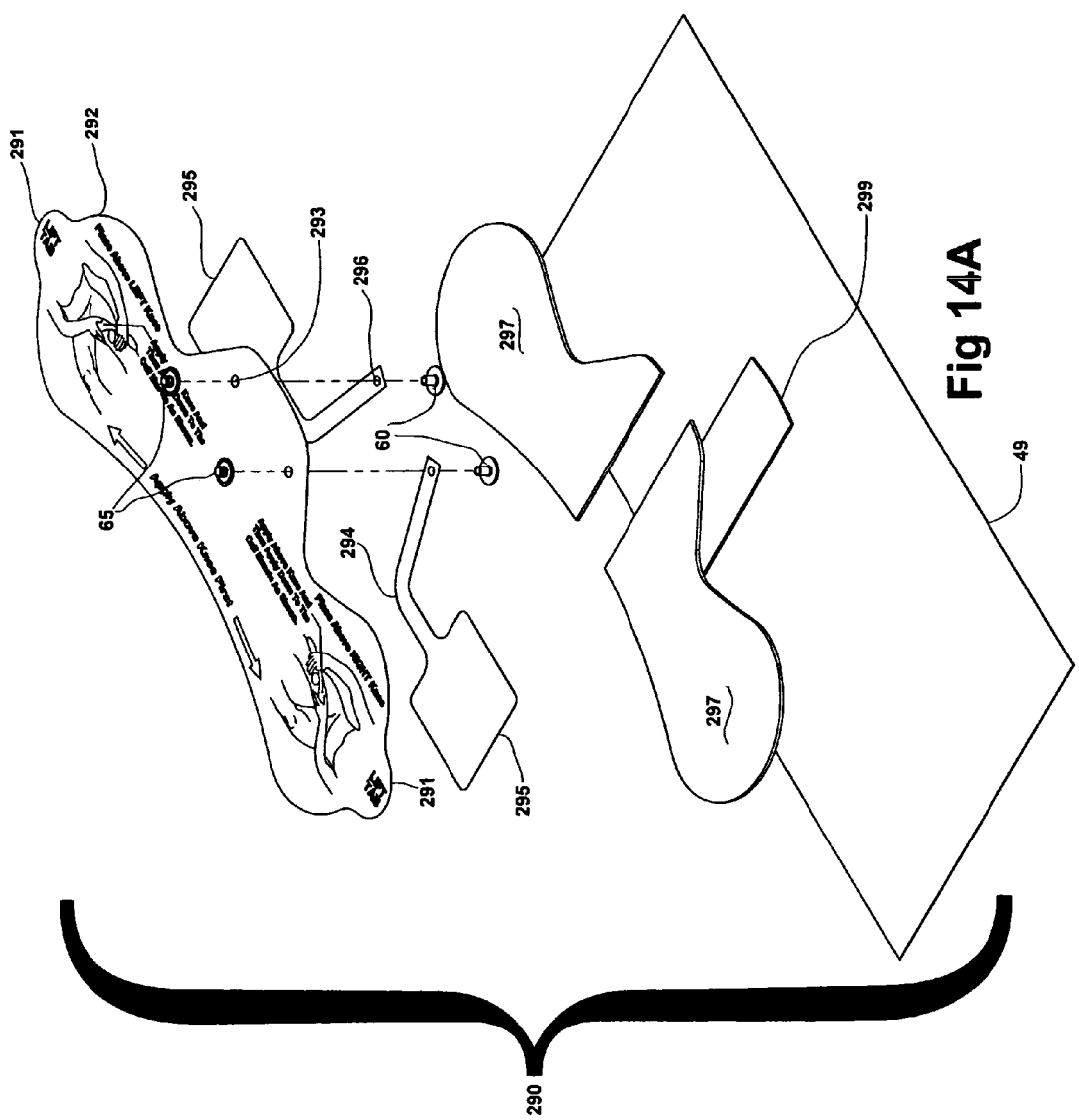
FIG. 14A is an exploded perspective view of a gel electrode patch configured for use diagonally about the knee of a patient.
Figure 14B:
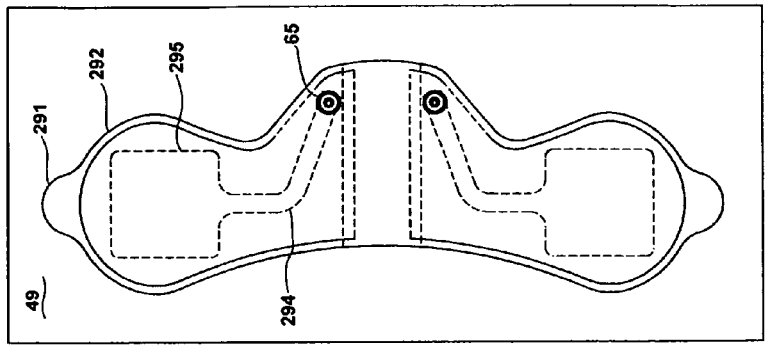
FIG. 14B is a top plan view of the patch of FIG. 14A showing in phantom the location of the patch components.

FIGS. 14A-C illustrate a third knee gel electrode patch 290 but one designed for application alongside the knee. The structure of the patch 290 is again similar with back sheet 49, fabric insulation 299, conductive gel sections 297, anchor posts 60 with upward extending post sections 62 passing through apertures 296 in legs 294 of conductive pads 295 and through apertures 293 in top sheet 292 until received in back recesses 69 of snaps 65. Top sheet 292 has lift tabs 291 at either end to facilitate placement and removal. As shown in the plan view of FIG. 14B, spacing between the gel sections 297 is about one inch and the conductive pads 295 have lengthy leg additions 294 to permit the spacing of snap 65 to remain at 1.7 inches. Finally, the printed art work 298 shown in FIG. 14C provides text and graphical information to advise the user upon the proper application of the electrode 290.

Figure 15B:
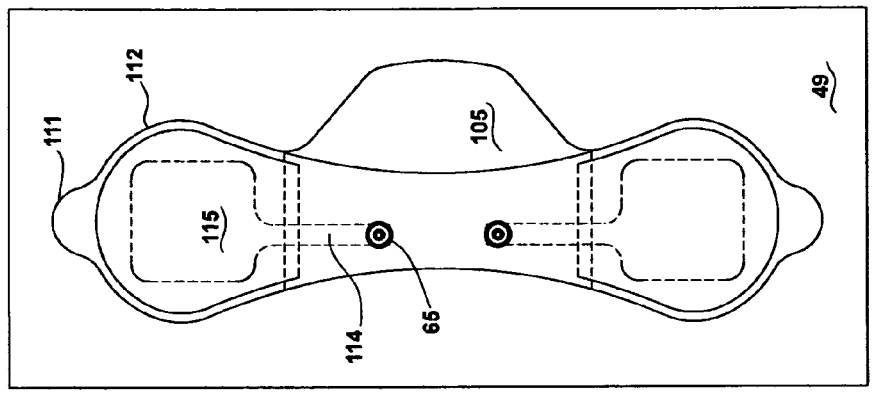
FIG. 15B is a top plan view of the patch of FIG. 15A showing in phantom the location of the patch components.
Figure 15A:
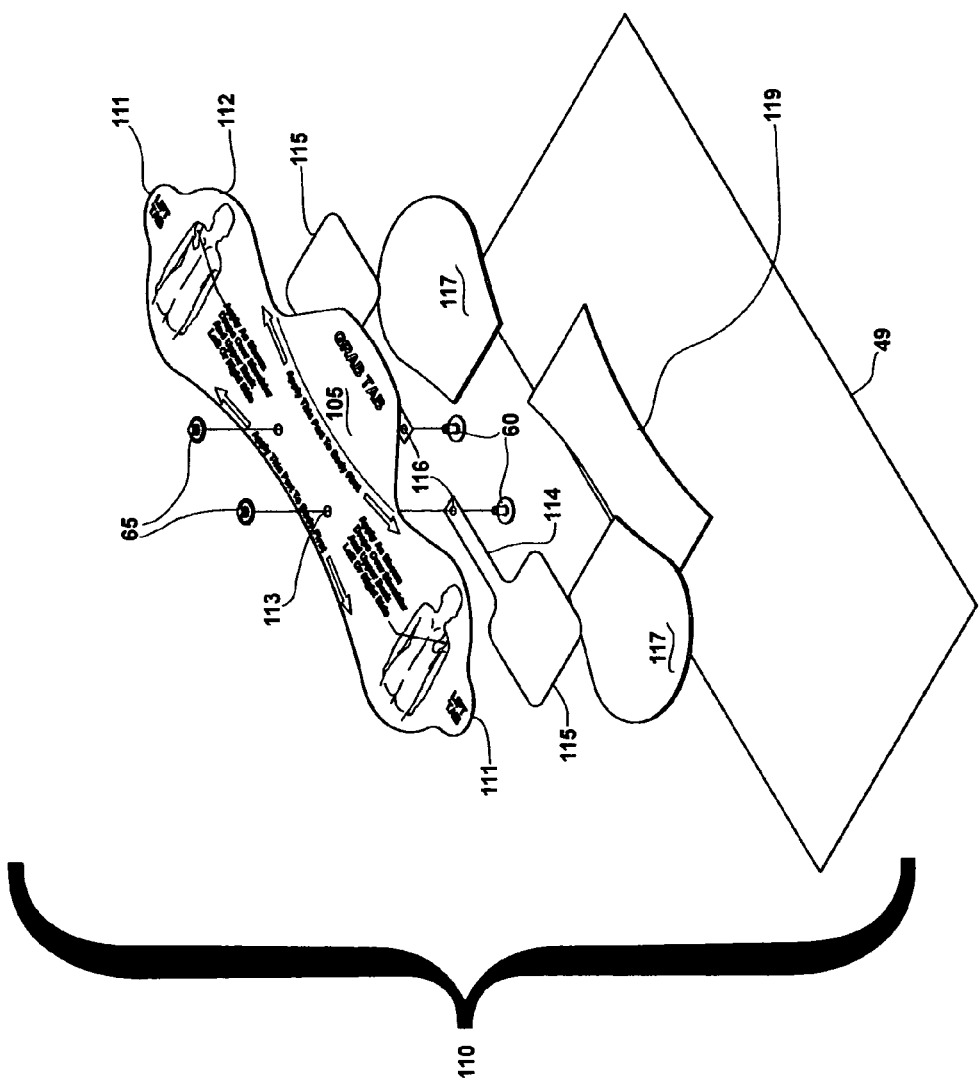
FIG. 15A is an exploded perspective view of a gel electrode patch configured for use about the shoulder and back of a patient.
Figure 15C:
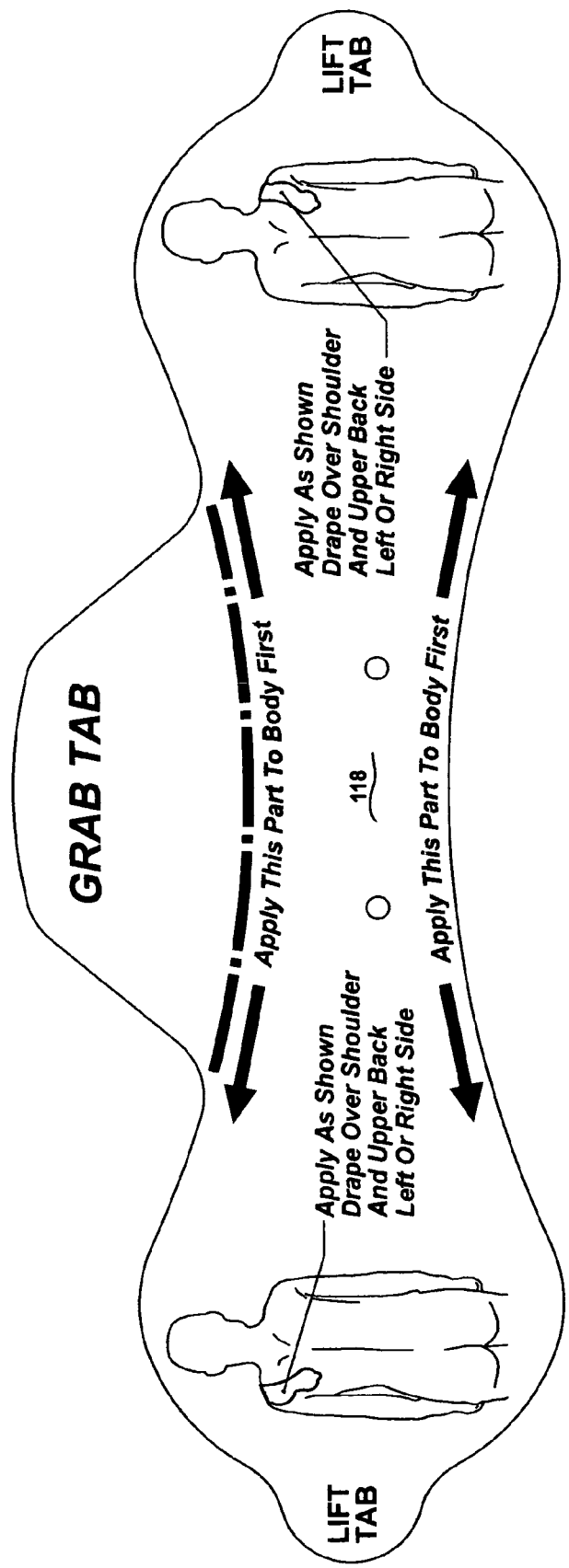
FIG. 15C is a top plan view of the art work imprinted upon the top sheet of the patch of FIG. 15A.

FIGS. 15A-C illustrate a compact gel electrode patch 190 designed for use on the shoulder and back. The structure of the patch 110 is again similar with back sheet 49, fabric insulation 119, conductive gel sections 117, anchor posts 60 with upward extending post sections 62 passing through apertures 116 in legs 114 of conductive pads 115 and through apertures 193 in top sheet 192 until received in back recesses 69 of snaps 65. The top sheet 112 has lift tabs 111 at either end extending beyond the gel sections 117 to facilitate placement and removal. Another larger tab portion 105 also facilitates application of the central section of the pad 110 first so that a good fit is more easily obtained. As shown in the plan view of FIG. 15B, spacing between the gel sections 117 is about one inch and the conductive pads 115 have leg additions 114 to permit the spacing of snap 65 to remain at 1.7 inches. Finally, the printed art work 118 shown in FIG. 15C provides text and graphical information to advise the user upon the proper application of the electrode 110.

Figure 16B:
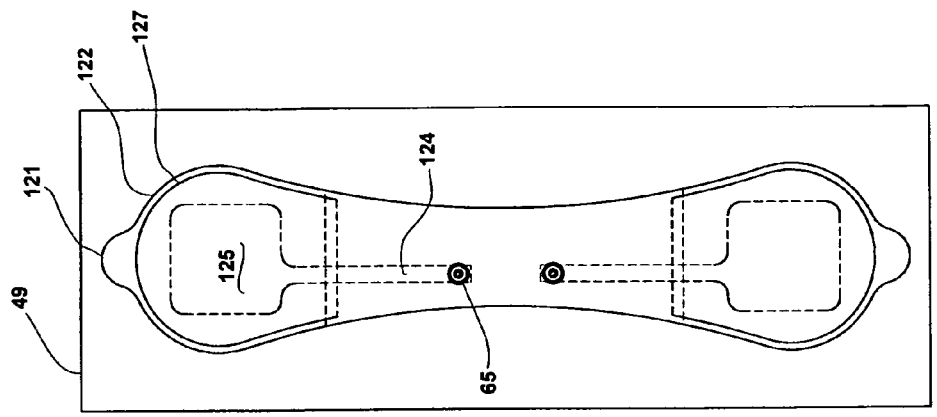
FIG. 16B is a top plan view of the patch of FIG. 16A showing in phantom the location of the patch components.
Figure 16A:
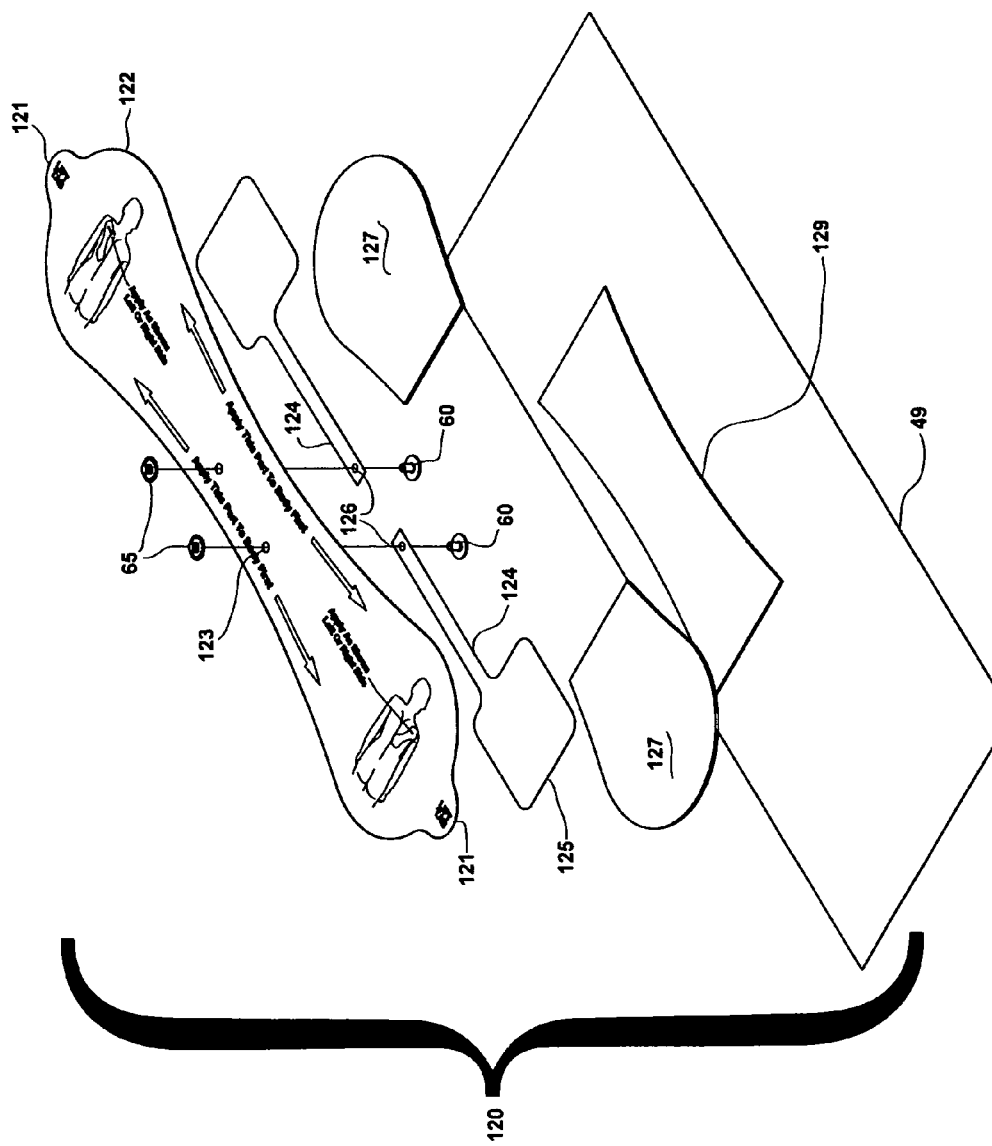
FIG. 16A is an exploded perspective view of a gel electrode patch configured in a relatively long construction for use on the back of a patient.
Figure 16C:
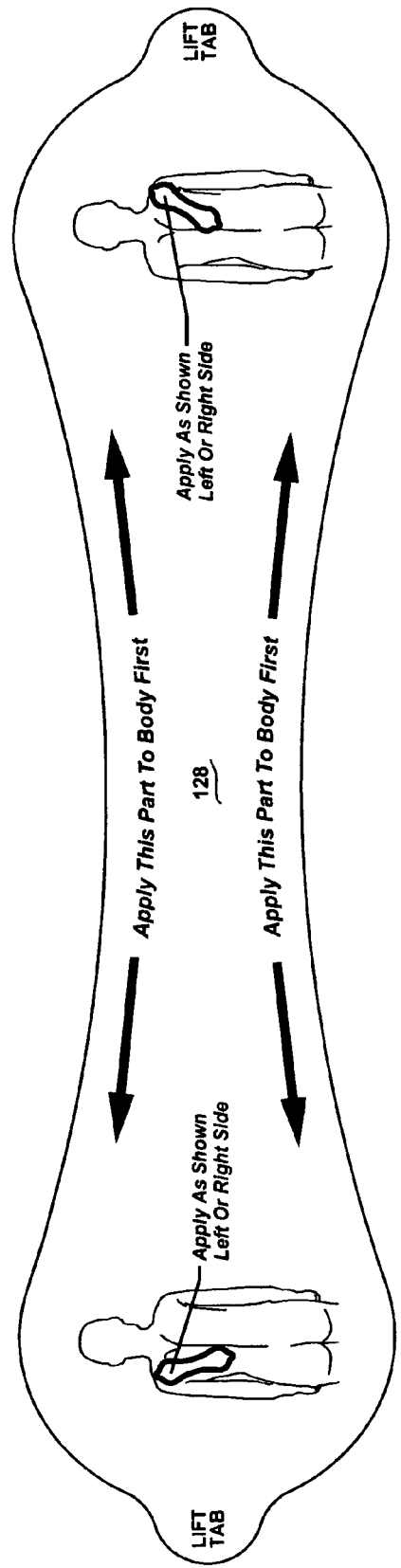
FIG. 16C is a top plan view of the art work imprinted upon the top sheet of the patch of FIG. 16A.

FIGS. 16A-C illustrate a second back gel electrode patch 120 but a larger one designed for use across the back. The structure of the patch 120 is again similar with back sheet 49, fabric insulation 129, conductive gel sections 127, anchor posts 60 with upward extending post sections 62 passing through apertures 126 in conductive pads 125 and through apertures 123 in top sheet 122 until received in back recesses 69 of snaps 65. As shown in the plan view of FIG. 16B, spacing between the gel sections 127 is about six inches and the conductive pads 125 have leg additions 124 to permit the spacing of snap 65 to remain at 1.7 inches. Finally, the printed art work 128 shown in FIG. 16C provides text and graphical information to advise the user upon the proper application of the electrode 120.

Figure 17B:
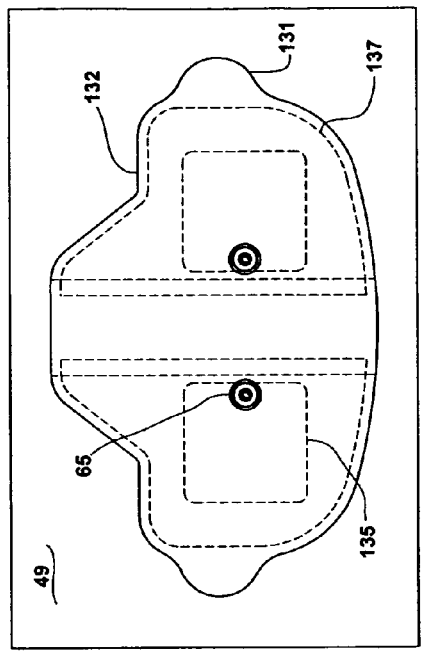
FIG. 17B is a top plan view of the patch of FIG. 17A showing in phantom the location of the patch components.
Figure 17A:
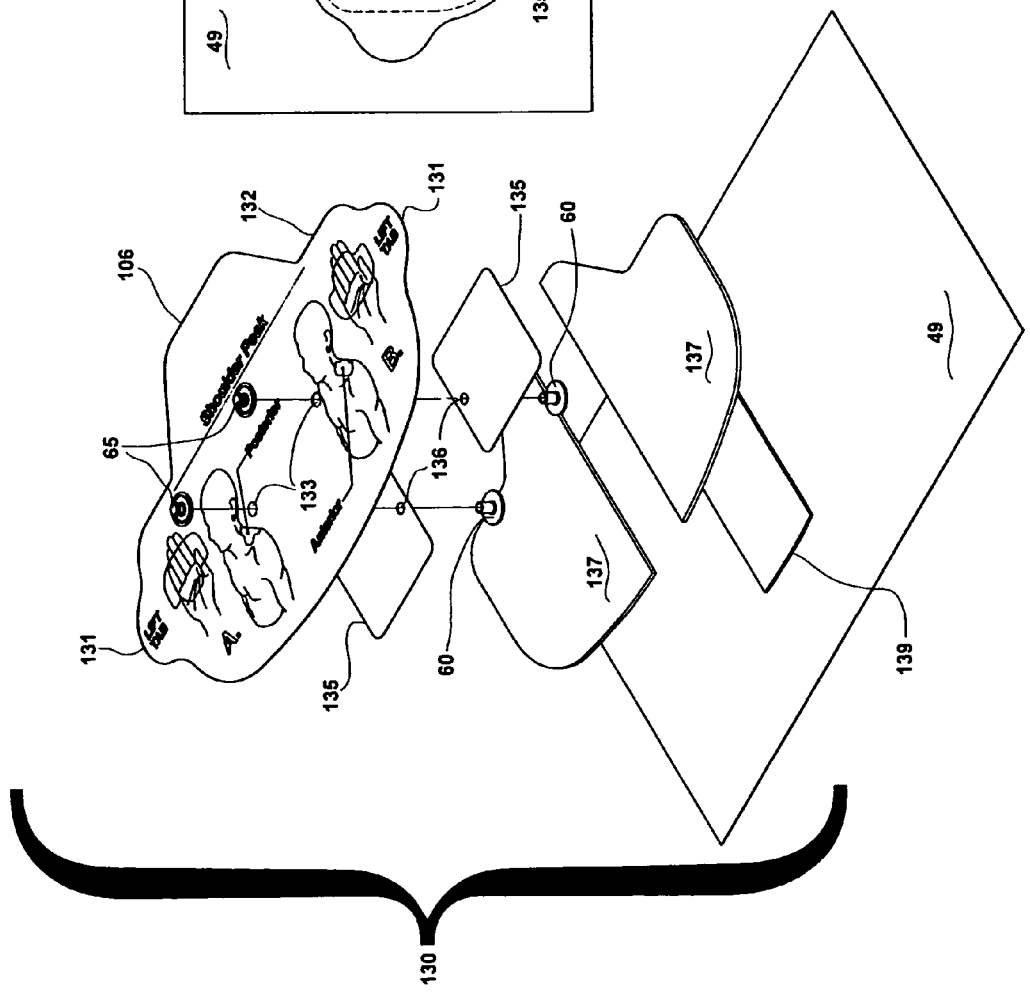
FIG. 17A is an exploded perspective view of a gel electrode patch configured for use on the shoulder or upper back of a patient.
Figure 17C:
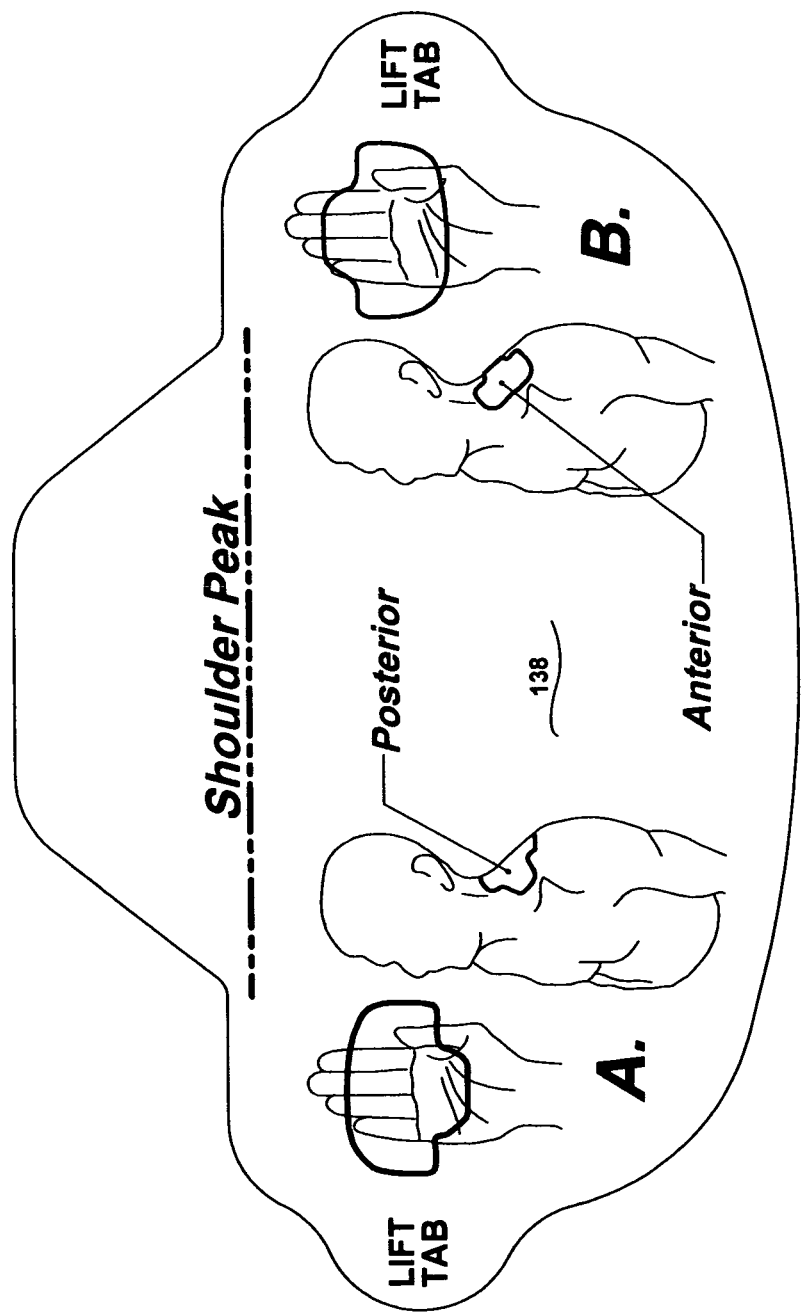
FIG. 17C is a top plan view of the art work imprinted upon the top sheet of the patch of FIG. 17A.

FIGS. 17A-C illustrate another gel electrode patch 130 but one designed to be positioned along the top of the shoulder. The structure of the patch 130 is again similar with back sheet 49, fabric insulation 139, conductive gel sections 137, anchor posts 60 with upward extending post sections 62 passing through apertures 136 in conductive pads 135 and through apertures 133 in top sheet 132 until received in back recesses 69 of snaps 65. At the ends of the top sheet 132 are lift tabs 131 to facilitate placement and removal and along one side is a larger tab 106 to aid in placement over the shoulder. As shown in the plan view of FIG. 17B, spacing between the gel sections 137 is approximately one inch. Finally, the printed art work 138 shown in FIG. 17C provides text and graphical information to advise the user upon the proper application of the electrode 130.

Figure 18C:
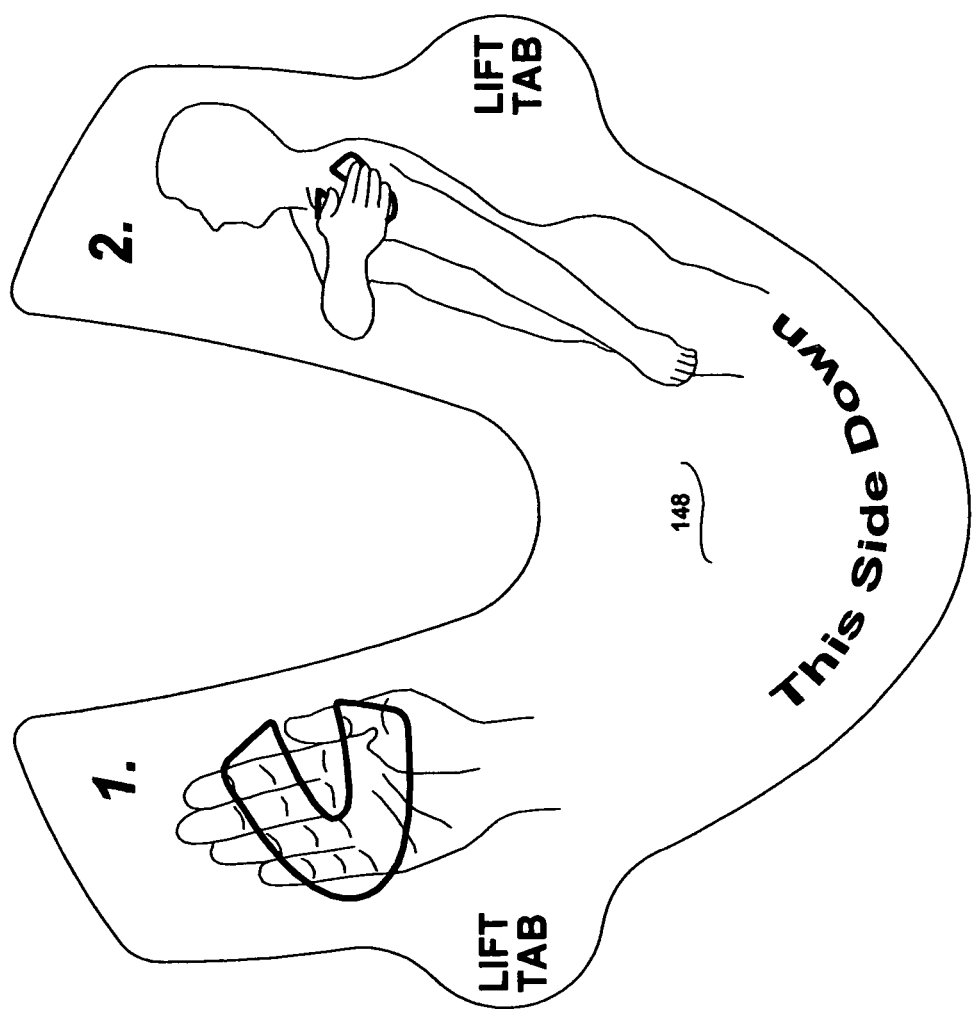
FIG. 18C is a top plan view of the art work imprinted upon the top sheet of the patch of FIG. 18A.

FIGS. 18A-C illustrates a second shoulder gel electrode patch 140 but one designed for a positioning on the upper arm. The structure of the patch 140 is again similar with back sheet 49, fabric insulation 149, conductive gel sections 147, anchor posts 60 with upward extending post sections 62 passing through apertures 146 in pads 145a, 145b and through apertures 143 in top sheet 142 until received in back recesses 69 of snaps 65. At the sides of the top sheet 142 are taps 141 to facilitate placement and removal. As shown in the plan view of FIG. 18B, spacing between the gel sections 147 is approximately one inch and the conductive pads 145a, 145b have leg additions 144a, 144b to permit the spacing of snap 65 to remain at 1.7 inches. Finally, the printed art work 148 shown in FIG. 18C provides text and graphical information to advise the user upon the proper application of the electrode 140.

Figure 19B:
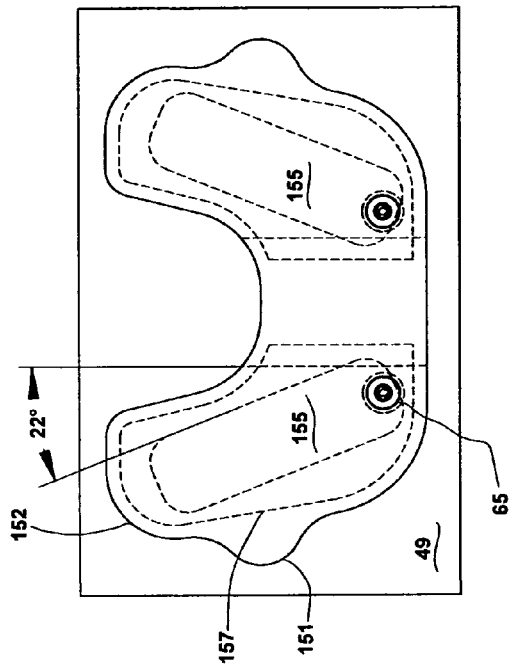
FIG. 19B is a top plan view of the patch of FIG. 19A showing in phantom the location of the patch components.
Figure 19A:
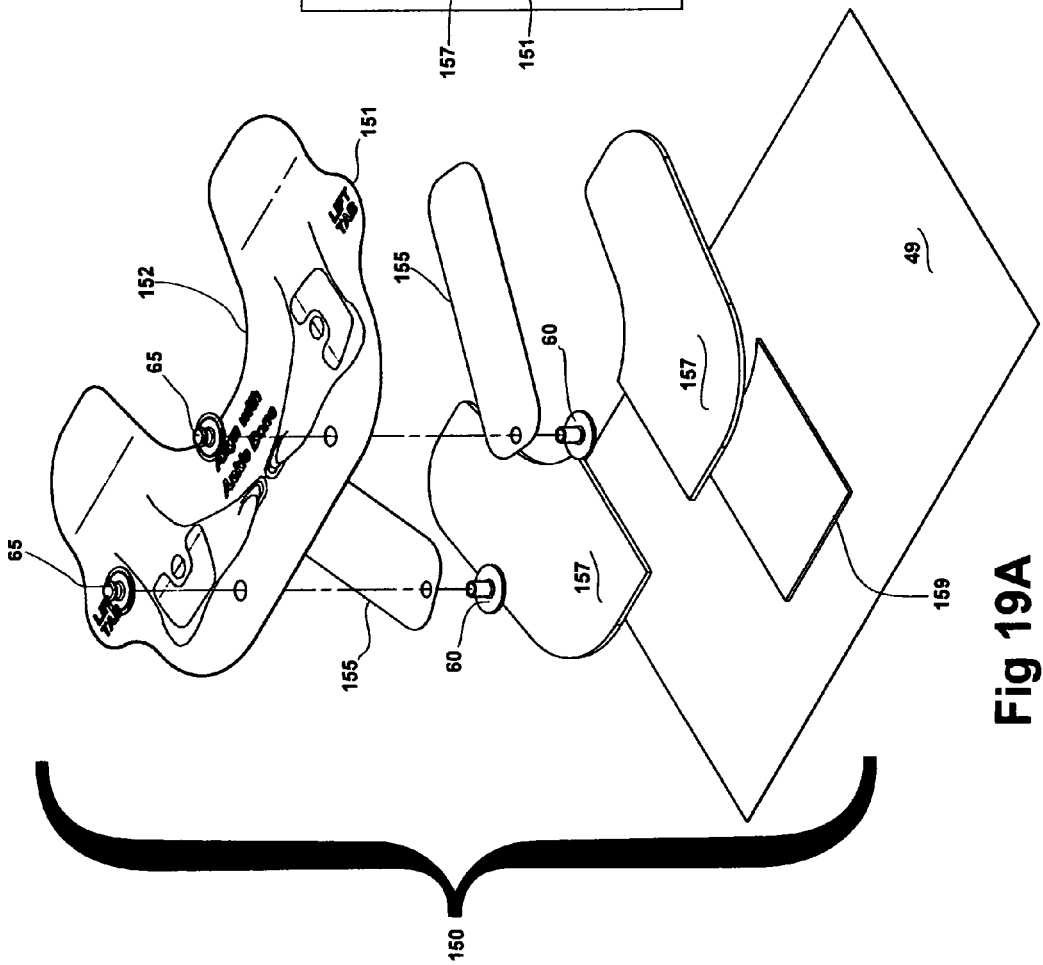
FIG. 19A is an exploded perspective view of a gel electrode patch configured for use about the ankle of a patient.
Figure 19C:
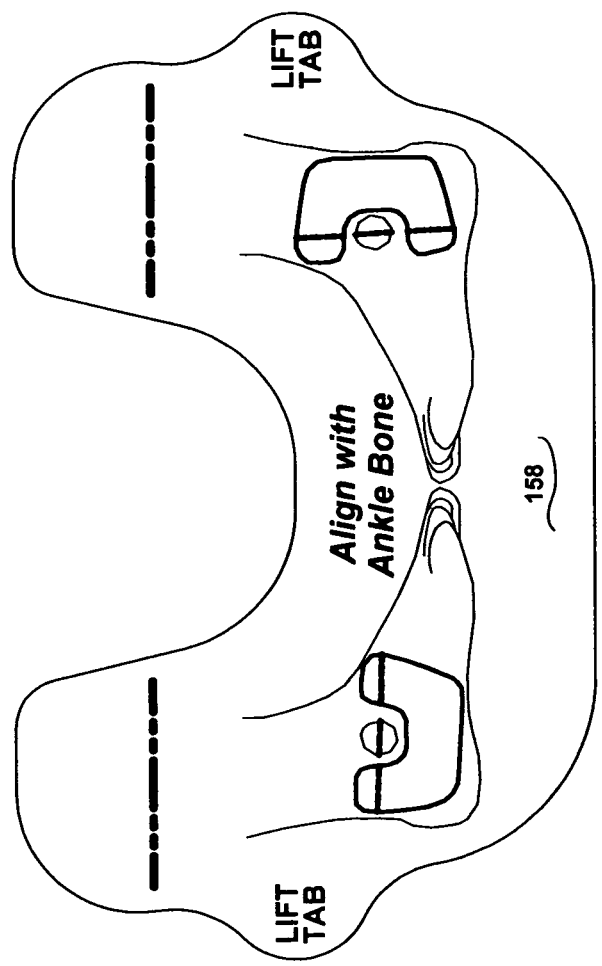
FIG. 19C is a top plan view of the art work imprinted upon the top sheet of the patch of FIG. 19A.

FIGS. 19A-C illustrate a gel electrode patch 150 designed for use at the ankle. The structure of the patch 150 is again similar with back sheet 49, fabric insulation 159, conductive gel sections 157, anchor posts 60 with upward extending post sections 62 passing through apertures 156 in conductive pads 155 and through apertures 153 in top sheet 152 until received in back recesses 69 of snaps 65. Lift tabs 151 on either side of the top sheet 151 aid in placement and removal. As shown in the plan view of FIG. 19B, spacing between the gel sections 157 is nearly one inch. Finally, the printed art work 158 shown in FIG. 19C provides text and graphical information to advise the user upon the proper application of the electrode 150.

Figure 20C:
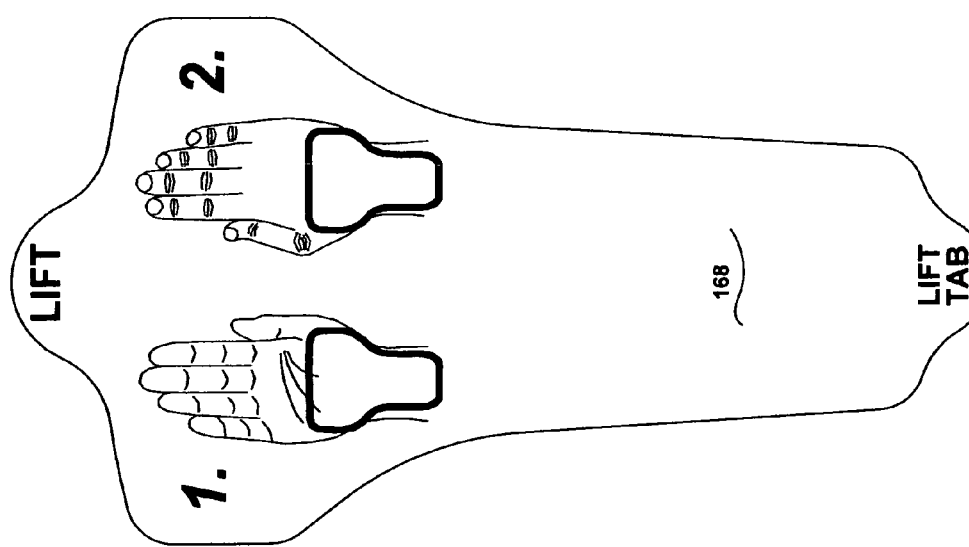
FIG. 20C is a top plan view of the art work imprinted upon the top sheet of the patch of FIG. 20A.

FIGS. 20A-C illustrate a gel electrode patch 160 designed use at the hand and wrist. The structure of the patch 160 is again similar with back sheet 49, fabric insulation 169, conductive gel sections 167a, 167b anchor posts 60 with upward extending post sections 62 passing through apertures 166 in conductive pads 165 and through apertures 163 in top sheet 162 until received in back recesses 69 of snaps 65. Lift tabs 161 at either end of the top sheet 162 aid in placement and removal. As shown in the plan view of FIG. 20B, spacing between the gel sections 167a, 167b is one inch and the conductive pad 165a has a leg addition 164 to permit the spacing of snaps 65 to remain at 1.7 inches. Finally, the printed art work 168 shown in FIG. 20C provides text and graphical information to advise the user upon the proper application of the electrode 160.

In use, it is generally recommended that the patient, or user, select the appropriate patch for the body location where pain treatment is to be administered. Then, the wearer should attach the power and control case 10 to the male snap elements 65 extending from the electrode patch. The backing sheet 49 can then be removed from the conductive gel surface of the conductive electrode patch and the patch and power and control case assembly applied to the users body as indicated by the graphic and textual instructions on the top surface of the patch. The power and control case can then be operated by pressing the on/off button 44 to activate the application of electro-stimulation to the body part and the intensity buttons 42, 43 may be utilized to adjust the strength of the electro-stimulation to the preferred level. The power and control system case 10 will then provide electro-stimulation therapy through the conductive surfaces of the patch. The user may leave the patch and power and control case 10 in place over the course of a day and deactivate administration or administer additional periods of therapy. Furthermore, the gel electrode patch may be removed after use and provided the surface is cleaned and the conductive gel is kept moist, the electrode patch may be reused over multiple days.

Furthermore, the power and control case 10 may be opened by depressing extending tabs 47 on the case top panel 40 and battery 32 may be replaced by the user if desired to extend the operative life of the power and control system. Alternatively, battery clip 30 may be slideably unlatched and removed from case 10 to replace the battery 32. However, it is also possible to provide the power and control case 10 in a sealed mode where battery replacement is not practical and patients are instead encouraged to replace the power system on a periodic basis.

Although preferred embodiments of the present invention have been disclosed in detail herein, it will be understood that various substitutions and modifications may be made to the disclosed embodiment described herein without departing from the scope and spirit of the present invention as recited in the appended claims.

I claim:

1. A first transcutaneous electrical neuro-stimulation gel pad electrode and a second transcutaneous electrical neuro-stimulation gel pad electrode each of the type having two tacky and conductive hydrogel sections separated by an insulator on a bottom surface, a top sheet, first and second conductive pads intermediate each of the two conductive hydrogel sections and the top sheet, first and second electrode leads connected to said first and second conductive pads;

wherein the first gel pad electrode has a top sheet with a first shape adapted for application to a first user body location and said top sheet has printed illustrations for electrode placement and orientation at said first user body location; and the second gel pad electrode has a top sheet with a second shape, different from said first shape, adapted for application to a second user body location and said top sheet has printed illustrations for electrode placement and orientation at said second user body location;

such that the distance between the first and second electrode leads on the first gel pad electrode is the same as the distance between the first and second electrode leads on the second gel pad electrode.

2. The transcutaneous electrical neuro-stimulation gel pad electrodes of claim 1 wherein the first shape of the first gel pad electrode is generally bean shaped with a protruding tab that is not coated with hydrogel and the printed illustrations are for grasping the first gel electrode and placement on the user lower back.

3. The transcutaneous electrical neuro-stimulation gel pad electrodes of claim 2 wherein the printed illustrations for the second gel electrode are for a second user body location selected from the group of knee, hip and upper arm.

4. The transcutaneous electrical neuro-stimulation gel pad electrodes of claim 1 wherein the electrode leads are snaps.

5. The transcutaneous electrical neuro-stimulation gel pad electrodes of claim 1 wherein the first shape at the first gel pad electrode is generally longitudinal with a tab at each end that is not coated with hydrogel.

6. The transcutaneous electrical neuro-stimulation gel pad electrodes of claim 1 wherein the first and second conductive pads of the first gel pad electrode have leg extensions to connect the conductive pads to the first and second electrode leads.

7. The transcutaneous electrical neuro-stimulation gel pad electrodes of claim 1 wherein the first conductive pad of the first gel pad electrode has a leg extension to connect the first conductive pad to the first electrode lead and the second conductive pad of the first gel pad electrode connects directly to the second electrode lead.

8. The transcutaneous electrical neuro-stimulation gel pad electrodes of claim 1 wherein the insulator on the bottom surface has a width of at least 0.75 inches between the two conductive hydrogel sections.

9. The transcutaneous electrical neuro-stimulation gel pad electrodes of claim 1 wherein the first and second electrode leads of the first gel pad electrode are connected to first and second electrical connections on a bottom of a power and control module, said first and second electrical connections being spaced apart by the same distance as the distance between the first and second electrode leads on the first gel pad electrode, so that when the electrode leads and electrical connections are connected the power and control module bottom is positioned adjacent to the top sheet of the first gel pad electrode as a combined unit and the combined unit of the first gel pad electrode and the power and control module is applied to a user's body location for self adhering attachment in accordance with the printed illustrations for electrode placement and orientation.

10. The transcutaneous electrical neuro-stimulation gel pad electrodes of claim 9 wherein a top of the power and control module has an increase intensity control encircled by a raised flange.

11. The transcutaneous electrical neuro-stimulation gel pad electrodes of claim 9 wherein the power and control module provides electro-stimulation therapy.

12. The transcutaneous electrical neuro-stimulation gel pad electrodes of claim 9 wherein the first and second electrical connections on the power and control module and the first and second electrode leads of the first gel pad electrode are female and male snaps.

13. The transcutaneous electrical neuro-stimulation gel pad electrodes of claim 9 wherein the power and control module comprises:
   a case having a top panel with an activation control, a visual indicia of activation, and an intensity increase control;
   a back panel having two openings, each providing access to an electrode connection, wherein said electrode connections are spaced apart by a first predetermined distance of between 0.8 and 2.0 inches; and
   a circuit board within the case in communication with both a plurality of switches operable to signal at least activation and current intensity and a battery, and having circuitry to produce at least one wave form.

14. The transcutaneous electrical neuro-stimulation gel pad electrodes of claim 9 wherein the dimensions of the power and control module are less than 2 inches by 3 inches with a thickness of less than 0.5 inches.

15. The transcutaneous electrical neuro-stimulation gel pad electrode of claim 9 wherein the distance between the first and second electrical connections on the bottom of the power and control module is between 0.8 and 2.0 inches.

16. The transcutaneous electrical neuro-stimulation gel pad electrodes of claim 9 wherein said electrodes are for placement for the relief of joint pain.

17. The transcutaneous electrical neuro-stimulation gel pad electrodes of claim 1 wherein the distance between the first and second electrode leads on the first gel pad is between 0.8 and 2.0 inches.

18. The transcutaneous electrical neuro-stimulation gel pad electrodes of claim 1 wherein said electrodes are for placement for the relief of joint pain.

* * * * *